(12) United States Patent
Isab et al.

(10) Patent No.: US 11,459,343 B2
(45) Date of Patent: *Oct. 4, 2022

(54) GOLD(I) N-HETEROCYCLIC CARBENE THIOUREA COMPLEX AND THERAPEUTIC COMPOSITIONS THEREOF

(71) Applicant: King Fahd University of Petroleum and Minerals, Dhahran (SA)

(72) Inventors: Anvarhusein A. Isab, Dhahran (SA); Adam A. A. Sulaiman, Dhahran (SA)

(73) Assignee: King Fahd University of Petroleum and Minerals, Dhahran (SA)

(*) Notice: Subject to any disclaimer, the term of this patent is extended or adjusted under 35 U.S.C. 154(b) by 0 days.

This patent is subject to a terminal disclaimer.

(21) Appl. No.: 16/773,414

(22) Filed: Jan. 27, 2020

(65) Prior Publication Data

US 2020/0299313 A1 Sep. 24, 2020

Related U.S. Application Data

(62) Division of application No. 16/359,306, filed on Mar. 20, 2019, now Pat. No. 10,544,165.

(51) Int. Cl.
*C07F 1/12* (2006.01)
*A61K 33/242* (2019.01)
*A61P 35/00* (2006.01)
*A61K 9/00* (2006.01)
*A61K 45/06* (2006.01)

(52) U.S. Cl.
CPC .............. *C07F 1/12* (2013.01); *A61K 9/0019* (2013.01); *A61K 33/242* (2019.01); *A61K 45/06* (2013.01); *A61P 35/00* (2018.01)

(58) Field of Classification Search
CPC .................................................. A61K 33/242
See application file for complete search history.

(56) References Cited

U.S. PATENT DOCUMENTS

| 9,573,967 | B2 | 2/2017 | Altaf | |
| 2020/0299311 | A1* | 9/2020 | Isab | A61P 35/00 |

FOREIGN PATENT DOCUMENTS

CN 105001244 A 10/2015

OTHER PUBLICATIONS

Liu, et al. ; C2-Symmetric Hindered "Sandwich" Chiral N-Heterocyclic Carbene Precursors and Their Transition Metal Complexes: Expedient Syntheses, Structural Authentication, and Catalytic Properties ; Organometallics, 37 (21) ; pp. 3576-3769 ; 2018 ; Abstract Only ; 3 Pages.

Marshall ; Endgroup and sidechain functionalization of surface-initiated ROMP thin _lms: progress towards ROMP-based molecular wires ; PhD Thesis ; 2018 ; 29 Pages.
Jiang, et al. ; Gold(I)-Catalyzed Selective Heterocyclization of Propargylic Thioureas: Mechanistic Study of Competitive Gold-Activation Mode ; Chemistry A European Journal ; Apr. 1, 2015 ; Abstract Only ; 3 Pages.
Zhdanko, et al. ; Coordination Chemistry of Gold Catalysts in Solution: A Detailed NMR Study ; Chemistry—A European Journal / vol. 18, Issue 46 ; Sep. 27, 2012 ; Abstract Only ; 10 Pages.
Hilf, et al. ; Thiol-functionalized ROMP polymers via Sacrificial Synthesis ; Macromolecules 42 (12) ; pp. 4127-4133 ; 2009 ; Abstract Only ; 2 Pages.
Rabbani, et al. ; Preparation of Tethered Palladium Catalysis Supported on Gold(111) and Its Surface Characterization by X-ray Photoelectron Spectroscopy (XPS) ; CSJ Journals vol. 81, Issue 8 ; 2016 ; Abstract Only ; 5 Pages.
Seliman, et al. ; Synthesis, X-ray structure and cytotoxicity evaluation of carbene-based gold(I) complexes of selenones ; ScienceDirect; Inorganica Chimica Acta, vol. 476 ; pp. 46-53 ; May 1, 2018 ; Abstract Only ; 3 Pages.
Seliman, et al. ; Synthesis, X-ray structure, DFT calculations and anticancer activity of a selenourea coordinated gold(I)-carbene complex ; ScienceDirect ; Polyhedron vol. 137 ; pp. 197-206 ; Nov. 24, 2017 ; Abstract Only ; 3 pages.
Seliman, et al. ; Synthesis, X-ray structures and anticancer activity of gold (I)-carbene complexes with selenones as co-ligands and their molecular docking studies with thioredoxin reductase ; ScienceDirect ; Journal of Organometallic Chemistry, vol. 848 ; Oct. 15, 2017 ; pp. 175-183 ; Abstract Only ; 4 Pages.
Mui, et al. ; Titanocene-Gold Complexes Containing N-Heterocyclic Carbene Ligands Inhibit Growth of Prostate, Renal, and Colon Cancers in Vitro ; Organometallics 35 (9) ; pp. 1218-1227 ; 2016 ; Abstract Only ; 2 Pages.
Fernandez-Gallardo, et al. ; Versatile synthesis of cationic N-heterocyclic carbine-gold (I) complexes containing a second ancillary ligand. Design of Heterobimetallic ruthenium-gold anticancer agents ; Chemical Communications Issue 16 ; 2016 ; Abstract Only ; 6 Pages.
Willwacher, et al. ; Total Synthesis, Stereochemical Revision, and Biological Reassessment of Mandelalide A: Chemical Mimicry of Intrafamily Relationships ; Chemistry—A European Journal / vol. 21, Issue 29 ; Jun. 10, 2015 ; Abstract Only ; 8 Pages.
Altaf, et al. ; Synthesis, X-ray structures, spectroscopic analysis and anticancer activity of novel gold(I) carbene complexes ; Science Direct ; Journal of Organometallic Chemistry, vol. 765 ; pp. 68-79 ; Aug. 15, 2014 ; Abstract Only ; 3 Pages.
Cisnetti, et al. ; Metal/N-Heterocyclic Carbene Complexes: Opportunities for the Development of Anticancer Metallodrugs ; Angewandte Chemie International Edition / vol. 52, Issue 46 ; Oct. 2, 2013 ; pp. 2269-2269 ; Abstract Only ; 2 Pages.

* cited by examiner

*Primary Examiner* — Rei Tsang Shiao
(74) *Attorney, Agent, or Firm* — Oblon, McClelland, Maier & Neustadt, L.L.P.

(57) ABSTRACT

The invention is directed to a method of treatment of proliferative diseases or disorders such as cancer with gold (I) N-heterocyclic carbene (NHC) thiourea or substituted thiourea complexes, to the complexes per se and to therapeutic compositions containing these gold(I) based complexes.

8 Claims, 23 Drawing Sheets

Specification includes a Sequence Listing.

Expression of Caspase 3

Complex (1)

Complex (2)

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: CASP9 forward primer

<400> SEQUENCE: 1
atgatcgagg acatccagcg                                                  20

<210> SEQ ID NO 2
<211> LENGTH: 20
<212> TYPE: DNA
<213> ORGANISM: Artificial Sequence
<220> FEATURE:
<223> OTHER INFORMATION: CASP9 reverse primer

<400> SEQUENCE: 2
ctgggtgttt ccggtctgag                                                  20

<210> SEQ ID NO 3
<211> LENGTH: 21
<212> TYPE: DNA
<213> ORGANISM: Artificial Sequence
<220> FEATURE:
<223> OTHER INFORMATION: CASP3 forward primer

<400> SEQUENCE: 3
ctcggtctgg tacagatgtc g                                                21

<210> SEQ ID NO 4
<211> LENGTH: 22
<212> TYPE: DNA
<213> ORGANISM: Artificial Sequence
<220> FEATURE:
<223> OTHER INFORMATION: CASP3 reverse primer

<400> SEQUENCE: 4
acttctacaa cgatcccctc tg                                               22

<210> SEQ ID NO 5
<211> LENGTH: 25
<212> TYPE: DNA
<213> ORGANISM: Artificial Sequence
<220> FEATURE:
<223> OTHER INFORMATION: ACTB forward primer

<400> SEQUENCE: 5
tcacccacac tgtgcccatc tacga                                            25

<210> SEQ ID NO 6
<211> LENGTH: 25
<212> TYPE: DNA
<213> ORGANISM: Artificial Sequence
<220> FEATURE:
```

```
<223> OTHER INFORMATION: ACTB reverse primer

<400> SEQUENCE: 6
cagcggaacc gctcattgcc aatgg                                    25
```

GOLD(I) N-HETEROCYCLIC CARBENE THIOUREA COMPLEX AND THERAPEUTIC COMPOSITIONS THEREOF

CROSS-REFERENCE TO RELATED APPLICATIONS

The present application is a Divisional of Ser. No. 16/359,306, now U.S. Pat. No. 10,544,165, having a filing date of Mar. 20, 2019, incorporated herein by reference in its entirety.

STATEMENT OF FUNDING ACKNOWLEDGEMENT

This research was supported by the King Fand University and Minerals (KFUPM) Research Committee under project No. IN171005.

REFERENCE TO A SEQUENCE LISTING

In accordance with 37 CFR § 1.52(e)(5), the present specification makes reference to a Sequence Listing submitted electronically as a .txt file named "528180US_ST25.txt" on Feb. 19, 2020. The .txt file was generated on Feb. 19, 2020 and is 1.42 kb in size. The entire contents of the Sequence Listing are herein incorporated by reference.

BACKGROUND OF THE INVENTION

Field of the Invention

The invention falls within the field of medicine as directed to treatment of proliferative diseases or disorders such as cancer with gold(I) N-heterocyclic carbene (NHC) thiourea or substitute thiourea complexes and to therapeutic compositions containing these gold(I) based complexes.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Metal-based pharmaceutical agents (Pd, Pt, Cu, Au, Ag) have been documented for their usefulness as antimicrobial and anticancer drugs. Among them, gold complexes have recently demonstrated significant biological activities and have been used to develop novel therapeutic agents. See V. Gandin, F. Tisato, A. Dolmella, M. Pellei, C. Santini, M. Giorgetti, C. Marzano, M. Porchia, and C. S. Uniti, "In Vitro and in Vivo Anticancer Activity of Copper(I) complexes with homoscorpionate tridentate tris(pyrazolyl)borate and auxiliary monodentate phosphine ligands," *J. Med. Chem.*, 2014, 12(57), 4745-60; P. Bippus, M. Skocic, M. A. Jakupec, B. K. Keppler, F. Mohr, "Synthesis, structures and in vitro cytotoxicity of some cationic cis-platinum(II) complexes containing chelating thiocarbamates," *J. Inorg. Biochem.*, 2011, 105(3), 462-466; W. Liu, K. Bensdorf, M. Proetto, U. Abram, A. Hagenbach, R. Gust, "NHC gold halide complexes derived from 4,5-diarylimidazoles: synthesis, structural analysis, and pharmacological investigations as potential antitumor agents," *J. Med. Chem.*, 2011, 54, 8605-8615; and J. Carlos, L. Rodriguez, "Phosphine-gold(I) compounds as anticancer agents: general description and mechanisms of action," *Anti-Cancer. Agent. Med. Chem.*, 2011, 11, 921-928, each incorporated herein by reference in their entirety. N-heterocyclic carbene (NHC) is a versatile derivative and its metal complexes have emerged as a focus of research for the development of catalysts and metallo-drugs due to their high stability. See C. Abbehausen, E. J. Peterson, R. E. De Paiva, P. P. Corbi, A. L. B. Formiga, Y. Qu, N. P. Farrell, "Gold(I)-phosphine-N-heterocycles: biological activity and specific (ligand) interactions on the C-terminal HIVNCp7 Zinc Finger," *Inorg Chem.*, 2013, 52, 11280-11287; H. D. Velazquez, F. Verpoort, "N-Heterocyclic carbene transition metal complexes for catalysis in aqueous media.," *Chem. Soc. Rev.*, 2012, 41(21), 7032-60; E. Schuh, P. Carolin, A. Citta, A. Folda, M. P. Rigobello, A. Bindoli, A. Casini, F. Mohr, "Gold(I) carbene complexes causing thioredoxin 1 and thioredoxin 2 oxidation as potential anticancer agents, "*J. Med Chem.*, 2012, 55, 5518-5528; X. Xu, S. H. Kim, X. Zhang, A. K. Das, H. Hirao, S. H. Hong, "Abnormal N-heterocyclic carbene gold(I) complexes: synthesis, structure, and catalysis in hydration of alkynes," *Organometallics*, 2013, 32, 164-171; M. K. Samantaray, C. Dash, M. M. Shaikh, K. Pang, R. J. Butcher, P. Ghosh, N. York, U. States, "Gold (III) N-heterocyclic carbene complexes mediated synthesis of β-enaminones from 1,3-Dicarbonyl compounds and aliphatic amines," *Inorg. Chem.*, 2011, 50, 1840-1848; F. K. Keter, I. A. Guzei, J. Darkwa, "N-heterocyclic dithiocarbamate platinum(II) complexes: unexpected transformation of dithiocarbamate to oxodithiocarbonate in phosphinoplatinum complexes in solution," *Inorg. Chem. Commun.*, 2013, 27, 60-63; D. G. Correia, F. E. Kuhn, B. Dominelli, "Medicinal applications of gold(I/III)-based complexes bearing N-heterocyclic carbene and phosphine ligands," *J. Organomet. Chem.*, 2018, 866, 153-164; and C. Zhang, M. Maddelein, R. W. Sun, H. Gornitzka, O. Cuvillier, C. Hemmert, "European journal of medicinal chemistry pharmacomodulation on gold-NHC complexes for anticancer applications e is lipophilicity the key point?," *Eur. J. Med. Chem.*, 2018, 157, 320-332, each incorporated herein by reference in their entirety.

L-ergothioneine is a thione-containing amino acid which naturally occurs in the body. It performs important biological functions as an antioxidant and exists in two tautomeric forms. L-ergothioneine forms complexes with several metal ions. See I. Erdelmeier, S. Daunay, R. Lebel, L. Farescour, J. Yadan, "Cysteine as a sustainable sulfur reagent for the protecting-group-free synthesis of sulfur-containing amino acids: biomimetic synthesis of L-ergothioneine in water" *Green Chem.*, 2012, 14, 2256-2265; D. P. Hanlox, "Interaction of ergothioneine with metal ions and metalloenzymes" *J. Med. Chem.*, 1971, 14, 1084-1087; and T. N. Motohashi, I. Mori, Y. Sugiura, H. Tanaka, "Metal Complexes of Egrothioneine," *Chem. Pharm. Bull.*, 1974, 22, 654-657, each incorporated herein by reference in their entirety.

Mitochondria generate a large quantity of oxygen species (ROS) which are produced in the cells and which are used for death signals originating from intrinsic and extrinsic apoptosis. The biological activity of some gold compounds has been shown to be associated with mitochondria dysfunction, eventually leading to cancer cell death. For instance, reported gold(I)-NHC complexes possess different mechanisms of the mitochondrial programmed cell death. See P. J. Barnard, M. V. Baker, S. J. Berners-Price, D. A. Day, "Mitochondrial permeability transition induced by dinuclear gold(I)-carbene complexes: potential new antimitochondrial antitumour agents," *J. Inorg. Biochem.*, 2004, 98, 1642-1647; A. Nandy, S. K. Dey, S. Das, R. N. Munda, J. Dinda, K. Das Saha, "Gold(I) N-heterocyclic carbene complex inhibits mouse melanoma growth by p53 upregulation.," *Mol. Cancer,* 2014, 13(1), 57; and H. G. Raubenheimer, S. Cronje, "Carbene complexes of gold: preparation, medical application and bonding," *Chem. Soc. Rev.,* 2008, 37(9), 1998-2011, each incorporated herein by reference in their entirety.

An in vitro and in vivo study of thiourea coinage metal (Au, Ag, Cu) complexes was reported in which the Au(I) thiourea complex showed very high potent tight-binding inhibition towards thioredoxin reductase. See C. Che, K. Yan, C. Lok, and C. Che, "Gold(I) complex of N,N'-disubstituted cyclic thiourea with in vitro and in vivo anticancer properties—potent tight-binding inhibition of thioredoxin reductase," *Chem. Commun.,* 2010, 46(41), 7691-7693, incorporated herein by reference in its entirety. The use of thiourea moiety in drugs as a tyrosinase inhibitor by repositioning the thiourea-containing drugs through free nitrogen for intermolecular interaction was reported. See J. Choi, J. Jee, "Repositioning of thiourea-containing drugs as tyrosinase inhibitors," *Int. J. Mol. Sci.,* 2015, 16, 28534-28548, incorporated herein by reference in its entirety.

Recently, new studies of gold(I)-NHC complexes have reported showing anticancer activity. See 0. Dada, G. Sanchez-sanz, M. Tacke, X. Zhu, "Synthesis and anticancer activity of novel NHC-gold(I)-sugar complexes," *Tetrahedron Lett.,* 2018, 59(30), 2904-2908; and A. Molter, S. Kathrein, B. Kircher, F. Mohr, "Anti-tumour active gold(I), palladium(II) and ruthenium(II) complexes with thio- and selenoureato ligands: a comparative study," *Dalt. Trans.,* 2018, 47, 5055-5064, each incorporated herein by reference in their entirety. Altaf et al. synthesized a new class of gold(I)-NHC with dithiocarbamates complexes and evaluated their anticancer activity against A549, HCT15 and HeLa cell lines. See M. Altaf, M. Monim-ul-mehboob, A. A. Seliman, A. A. Isab, V. Dhuna, G. Bhatia, and K. Dhuna, "Synthesis, X-ray structures, spectroscopic analysis and anticancer activity of novel gold(I) carbene complexes," *J. Organomet. Chem.,* 2014, 765, 68-79, incorporated herein by reference in its entirety. Moreover, Özdemir et al. synthesized a series of gold(I)-NHC complexes. The complexes were evaluated for their antimicrobial activity against Gram-positive, Gram-negative bacteria, and fungal species. See I. Özdemir, N. Temelli, S. Gunal, S. Demir, "Gold(I) Complexes of N-heterocyclic carbene ligands containing benzimidazole: synthesis and antimicrobial activity," *Molecules,* 2010, 15(4), 2203-2210, incorporated herein by reference in its entirety.

Extrinsic apoptosis is initiated through transmembrane death receptors and the execution of these processes is mainly regulated by the BCL-2 and caspase proteins. See K. S. Danial N N, "No Title," *Cell death Crit. Control points,* vol. 116, no. 2, pp. 205-219, 2004; and L. Galluzzi, I. Vitale, J. M. Abrams, E. S. Alnemri, E. H. Baehrecke, M. V. Blagosklonny, T. M. Dawson, V. L. Dawson, W. S. El-Deiry, "Molecular definitions of cell death subroutines: recommendations of the nomenclature committee on cell death 2012," *Cell Death & Differentiation,* 2012, 19(1), 107-120, each incorporated herein by reference in their entirety. Activation of the BCL-2 family members results in the release of pro-apoptotic proteins, including cytochrome c, which ultimately activates the caspase family proteins. See M. C. Wei, T. Lindsten, V. K. Mootha, S. Weiler, A. Gross, M. Ashiya, C. B. Thompson, "tBID, a membrane-targeted death ligand, oligomerizes BAK to release cytochrome c," *Genes Dev.,* 2000, 14(16), 2060-71; M. C. Wei, W. X. Zong, E. H. Cheng, T. Lindsten, V. Panoutsakopoulou, A. J. Ross, K. A. Roth, G. R. MacGregor, C. B. Thompson, "Proapoptotic BAX and BAK: A requisite gateway to mitochondrial dysfunction and death," *Science* 2001, 292(5517), 727-730; and R. Eskes, S. Desagher, B. Antonsson, J-C. Martinou, "Bid induces the oligomerization and insertion of Bax into the outer mitochondrial membrane," *Mol. Cell Biol.,* 2000, 20(3), pp. 929-935, each incorporated herein by reference in their entirety. Then these effector caspases ultimately lead to the hallmarks of apoptosis, including DNA fragmentation, cell shrinkage and membrane blebbing. See M. Woo, R. Hakem, M. S. Soengas, G. S. Duncan, A. Shahinian, D. Kagi, A. Hakem, M. McCurrach, W. Khoo, "Essential contribution of caspase 3/CPP32 to apoptosis and its associated nuclear changes," *Genes Dev,* 1998, 12(6), 806-819, incorporated herein by reference in its entirety.

Gold compounds as inhibitors interact with thiol or selenol, the active site of methionine and Se-methionine, which are used as antioxidants to prevent human cancers. See M. Björnstedt, A. P. Fernandes, "Selenium in the prevention of human cancers," *J. EPMA,* 2010, 1(3), 389-95; H. Tapiero, D. Townsend, K. Tew, "The antioxidant role of selenium and seleno-compounds," *Biomed. Pharmacother.,* 2003, 57(3-4), 134-144; M. Navarro-Alarcon, C. Cabrera-Vique, "Selenium in food and the human body: a review.," *Sci. Total Environ.,* 2008, 400(1-3), 115-41; L. Letavayová, V. Vlcková, J. Brozmanová, "Selenium: from cancer prevention to DNA damage.," *Toxicology,* 2006, 227(1-2), 1-14; and R. Laplaza, V. Polo, J. Quero, S. Cabello, T. Fuertes, E. Cerrada, M. Concepcio, "Proteasome versus thioredoxin reductase competition as possible biological targets in antitumor mixed thiolate-dithiocarbamate gold(III) complexes," *Inorg. Chem.,* 2018, 57, 10832-10845, each incorporated herein by reference in their entirety. Also, glutathione peroxidase (GPx), thioredoxin (Trx), and the enzyme thioredoxin reductase (TrxR) are used to protect different organisms from damage due to the catalytic cycle reducing harmful peroxidase. See K. P. Bhabak, B. J. Bhuyan, G. Mugesh, "Bioinorganic and medicinal chemistry: aspects of gold(I)-protein complexes," *Dalt. Trans.,* 2011, 40, 2099-2111; S. E. Jackson-Rosario, W. T. Self, "Targeting selenium metabolism and selenoproteins: novel avenues for drug discovery.,"*Metallomics,* 2010, 2(2), 112-6; L. Oehninger, M. Stefanopoulou, H. Alborzinia, J. Schur, S. Ludewig, K. Namikawa, A. Muñoz-Castro, R. W. Köster, K. Baumann, S. Won W. S. Sheldrick, I. Ott, "Evaluation of arene ruthenium (II) N-heterocyclic carbene complexes as organometallics interacting with thiol and selenol containing biomolecules.," *Dalton Trans.,* 2013, 42(5), 1657-66; and J. L. Hickey, R. A. Ruhayel, P. J. Barnard, M. V Baker, S. J. Berners-price, A. Filipovska, "Mitochondria-Targeted Chemotherapeutics: The rational design of gold(I) N-heterocyclic carbene complexes that are selectively toxic to cancer cells and target protein selenols in preference to thiols," 2008, I, 12570-12571, each incorporated herein by reference in their entirety.

Previous studies evaluated the in vitro cytotoxicity against different cancer cell lines and molecular docking with DNA of a series of gold(I) N-hetero-cyclic carbenes with aliphatic and hydrocyclic selenone ligands, which have higher anticancer activity than cisplatin; see A. A. A. Seliman, M. Altaf, N. A. Odewunmi, A. Kawde, W. Zierkiewicz, S. Ahmad, S. Altuwaijri, A. A. Isab, "Synthesis, X-ray structure, DFT calculations and anticancer activity of a selenourea coordinated gold(I)-carbene complex," *Polyhedron,* 2017, 137, 197-206; A. A. A. Seliman, M. Altaf, A. T. Onawole, S. Ahmad, M. Yagoub, A. A. Al-saadi, S. Altuwaijri, G. Bhatia, J. Singh, A. A. Isab, "Synthesis, X-ray structures and anticancer activity of gold(I)-carbene complexes with selenones as co-ligands and their molecular docking studies with thioredoxin reductase," *J. Organomet. Chem.,* 2017, 848, 175-183; and A. A. A. Seliman, M. Altaf, A. T. Onawole, A. Al-saadi, S. Ahmad, A. Alhoshani, G. Bhatia, A. A. Isab, "Synthesis, X-ray structure and cytotoxicity evaluation of carbene-based gold(I) complexes of selenones," *Inorganica Chim. Acta,* 2018, 476, 46-53, each incorporated herein by reference in their entirety.

In view of the need for new anti-cancer agents and pharmacological options, as disclosed herein the inventors synthesized, characterized and showed that gold(I)-N-heterocyclic carbene (NHC) complexes exhibited potent cytotoxic activity against tumor cells.

BRIEF SUMMARY OF THE INVENTION

The invention involves a series of gold(I)-NHC complexes with thiourea or a substituted thiourea, such as dimethylthiourea; pharmaceutical compositions containing these complexes; and methods for inducing cytotoxicity or treating proliferative diseases, disorders or conditions such as cancer by administering these gold(I) complexes. The gold(I) complexes of the invention conform to Formula I below:

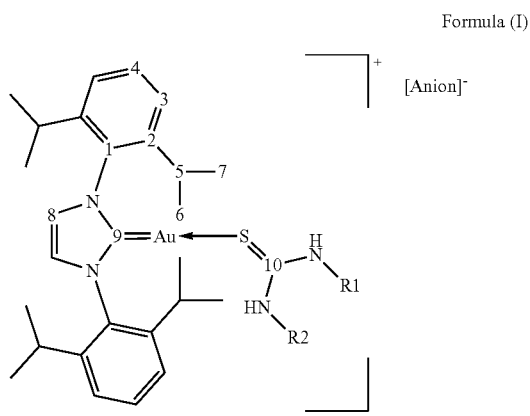

Formula (I)

wherein R1 and R2 are, independently, hydrogen, $C_{1-6}$ alkyl, $C_{2-6}$ alkenyl, $C_{2-6}$ alkynyl, or $C_{4-10}$ aryl and where the anion is $PF_6^-$ or another pharmaceutically acceptable anion.

The foregoing paragraph has been provided by way of general introduction, and is not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings below.

DETAILED DESCRIPTION OF THE INVENTION

Figure 1:
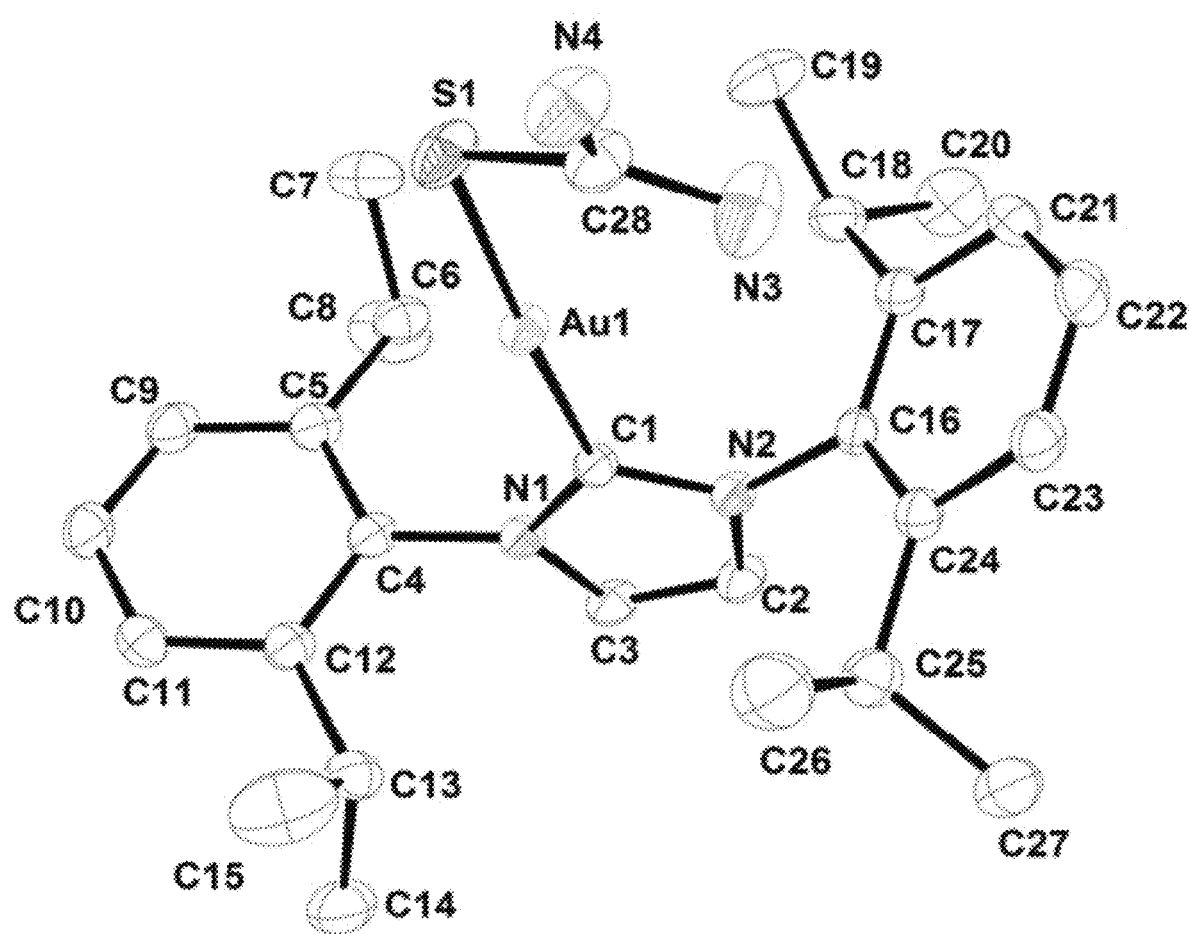
FIG. 1. Molecular structure of complex [Au(Ipr) (κSCN$_2$H$_4$)PF$_6$ (1), with labelling atoms and 50% probability ellipsoids level and without hydrogen atoms for clarity.

As used herein, the terms "compound" and "complex" are used interchangeably, and are intended to refer to a chemical entity, whether in a solid, liquid or gaseous phase, and whether in a crude mixture or purified and isolated.

As used herein, the term "substituted" refers to replacing at least one hydrogen atom of a molecule with a non-hydrogen functional group. Such non-hydrogen functional groups can independently include, for example, one or more of the following: alkyl, alkenyl, alkynyl and aryl.

As used herein, the term "alkyl" refers to a fully saturated branched, or unbranched hydrocarbon fragment, preferably for substitution at R1 and/or R2 of Formula (I) a $C_1$-$C_6$ alkyl.

Representative examples of such alkyl include, but are not limited to, methyl, ethyl, n-propyl, isopropyl, n-butyl, sec-butyl, iso-butyl, tert-butyl, n-pentyl, isopentyl, neopentyl, n-hexyl, isohexyl, 3-methylhexyl, 2,2-dimethylpentyl, 2,3-dimethylpentyl, n-heptyl, n-octyl, n-nonyl, n-decyl and the like.

The term "aryl", as used herein, includes aromatic monocyclic or multicyclic (e.g., tricyclic, bicyclic), hydrocarbon ring systems comprising or consisting of hydrogen and carbon atoms, where the ring systems may be partially saturated. Aryl groups include, but are not limited to, phenyl, tolyl, xylyl, biphenyl, naphthyl, anthracenyl, phenanthryl and tetralin. This term also includes substituted aryl and heteroaryl groups such as phenol, aryl halides or imidazyl preferably an $C_6$-$C_{10}$ aryl is chosen for substitution at R1 and R2 of Formula (I).

The term "halogen", as used herein, means fluoro, chloro, bromo and iodo.

The term "anion" means a negatively charged ion including, but not limited to, halides, such as fluoride, chloride, bromide, and iodide, nitrate, sulfate, phosphate, methanesulfonate, ethanesulfonate, p-toluenesulfonate, salicylate, malate, maleate, succinate, tartrate, citrate, acetate, perchlorate, trifluoromethanesulfonate, acetylacetonate, tetrafluoroborate, hexafluorophosphate, and hexafluoroacetylacetonate.

One aspect of the invention relates to a method for treating a proliferative disease, disorder or condition in a subject in need thereof that includes administering to the subject at least one complex comprising a gold atom coordinated with a thiourea that has the following chemical structure:

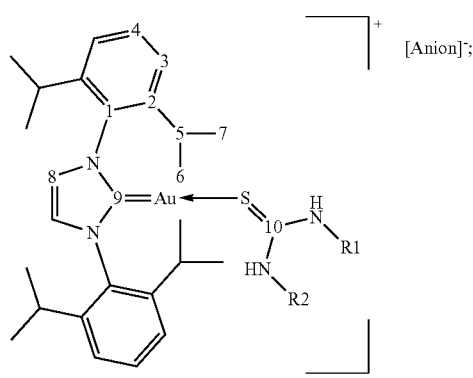

wherein R1 and R2 are, independently, hydrogen, $C_{1-6}$ alkyl, $C_{2-6}$ alkenyl, $C_{2-6}$ alkynyl, or $C_{6-10}$ aryl. These groups include $C_1$, $C_2$, $C_3$, $C_4$, $C_5$, or $C_6$ alkyl; $C_2$, $C_3$, $C_4$, $C_5$, or $C_6$ alkenyl; and C, $C_2$, $C_3$, $C_4$, $C_5$, or $C_6$ alkynyl, which may be further substituted, for example, with one or more alkyl, alkenyl, alkynyl, halogen, or hydroxyl groups. Advantageously, this method may involve administering a complex such as complex (1) wherein R1 and R2 are each hydrogen or a complex such as complex (2) wherein R2 and R2 are each methyl.

Any pharmaceutically acceptable anion may for a part of the complex of Formula 1 including fluoride, chloride, iodide, hexaflurophosphate ("$PF_6^-$"), or triflate.

Surprisingly, in view of the relatively lower activity of thio-based complexes compared to seleno-based complexes as reported by Molter, et al., *Dalt. Trans.*, 2018, 47, 5055-5064, the inventors found that the gold(I) thiourea complexes of the invention exhibited high degrees of antiproliferative and cytotoxic activity as shown in the Examples.

While not being bound to any particular theory, the inventors believe that use of thio-based complexes may overcome problems associated with interaction of other kinds of gold(I) complexes with serum albumin which may act as a gold(I) complex scavenger.

As used herein the terms "subject" and "patient" may be used interchangeably.

A subject treated with a gold(I) complex of the invention may have a proliferative disease, disorder or condition such as cancer including sarcoma, carcinoma, lymphoma, or a germ cell tumor. Other types of cancer which may be treated using this method include cervical cancer, bone cancer, colon cancer, testicular cancer, germ cell cancer, cervical cancer, bladder cancer, head and neck cancer, esophageal cancer, lung cancer, mesothelioma, a brain tumor or neuroblastoma. Other types of cancer or proliferative diseases that are currently treated with platinum-based drugs such as cisplatin may be treated with a gold(I) complexe as disclosed herein.

In some embodiments the subject is at least 0, 1, 2, 3, 4, 5, 10, 15, 20, 25, 30, 35, 40, 45, 50, 55, 60, 65, 70, 75, 80, 85, 90 or >90 years of age. A subject may be male or female and may have a newly diagnosed disease, disorder or condition, be currently under treatment, or suffer from a relapsing or chronic disease, disorder or condition. A subject may be someone who has lost or is losing responsiveness to another treatment, such to a cancer treatment with cisplatin or another platinum-based anticancer agent. A subject may have a comorbid condition such as diabetes, heart disease, hypertension (high blood pressure), hyperlipidemia (high cholesterol) and peripheral vascular disease.

A subject may have experienced one or more side-effects of another kind of treatment, such as side-effects to a cancer treatment with cisplatin or another platinum containing anticancer agent. Side effects include one or more of the following: bone marrow suppression, neurotoxicity, ototoxicity or hearing problems, nephrotoxicity or kidney problems, electrolyte disturbance, nausea, vomiting, numbness, trouble walking, allergic reactions, electrolyte problems including hypomagnesaemia, hypokalaemia and hypocalcaemia, and/or heart disease.

Those skilled in the art can determine a suitable mode for administering a gold (I) complex of the invention based on patient status, type of disorder, disease or condition, or anatomical location of cells associated with the disorder, disease or condition. Advantageously for treatment of many types of cancer, the gold (I) complex will be administered intravenously or intraperitoneally. Other modes of administration include those that bring the gold complexes into contact with target cells, such as into contact with proliferating cancer or tumor cells. These modes include oral and parenteral administration. Administration may be targeted to a specific site or anatomical compartment containing cancer cells including into a solid cancer or into the vasculature or other compartments for a non-solid cancer. Other modes of administration include intravesical, intradermal, transdermal, subcutaneous, intramuscular, intralesional, intracranial, intrapulmonal, intracardial, infrasternal and sublingual modes.

In some embodiments, a gold complex of the invention may be administered as the only active agent. In other embodiments, more than one type of gold complex of the invention, such as a cocktail containing both complex (1) and complex (2), may be administered.

In still other embodiments, one or more gold complexes of the invention may be administered in conjunction with another agent, such as another anti-cancer drug used to treat ovarian cancer, biliary tract cancer, lung cancer (diffuse malignant pleural mesothelioma), gastric cancer, carcinoma of salivary gland origin, breast, colon, lung, prostate, melanoma and pancreatic cancer cell lines, squamous cell carcinoma of male genital tract, urothelial bladder cancer, or cervical cancer; or with at least one drug such as paclitaxel, paclitaxel and 5-FU, UFT (tegafur/uracil), doxorubicin, cyclophosphamide and doxorubicin, gemcitabine, osthold, honeybee venom, anvirzel, or beaciozumab.

Other embodiments of the invention include the gold complexes, per se, as well as compositions, such as those containing one or more gold complexes as disclosed herein and encompassed by Formula (I) in combination with a pharmaceutically acceptable excipient or carrier or in combination with another active agent. Typically, a pharmaceutical composition containing a gold(I) complex is sterile, isotonic, and otherwise suitable for administration to a patient.

As used herein, the term "composition" refers to a mixture of the active ingredient with other chemical components, such as pharmaceutically acceptable carriers and excipients. The composition may be manufactured using any of a variety of processes, including, without limitation, conventional mixing, dissolving, granulating, levigating, emulsifying, encapsulating, entrapping, and lyophilizing. The pharmaceutical composition can take any of a variety of forms including, without limitation, a sterile solution, suspension, emulsion, lyophilisate, tablet, pill, pellet, capsule, powder, syrup, elixir or any other dosage form suitable for administration.

As used herein, the term "active ingredient" refers to an ingredient in the composition that is biologically active, for example, the gold(I) complex of Formula (I), a salt thereof, a solvate thereof, a tautomer thereof, and a stereoisomer thereof.

As used herein, the phrase "pharmaceutically acceptable carrier or excipient" refers to a pharmaceutically acceptable material, composition or vehicle such as a liquid or solid filler, diluent, binder, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient.

Exemplary materials which can serve as pharmaceutically acceptable carriers include, but are not limited to: (1) sugars, such as lactose, glucose and sucrose; (2) starches, such as corn starch and potato starch; (3) cellulose, and its derivatives, such as sodium carboxy methyl cellulose, ethyl cellulose and cellulose acetate; (4) powdered tragancanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) other non-toxic compatible substances employed in pharmaceutical formulations and mixtures thereof. Non-limiting examples of specific uses of pharmaceutically acceptable carriers can be found in, e.g. "Pharmaceutical Dosage Forms and Drug Delivery Systems" (Howard C. Ansel et al., eds., Lippincott Williams & Wilkins Publishers, 11$^{th}$ edition, 2017; ISBN-13: 978-1496347282); "Remington: The Science and Practice of Pharmacy" (Alfonso R. Gennaro ed., Lippincott, Williams & Wilkins, 21$^{th}$ edition 2005; 0-7817-4673-6); "Goodman & Gilman's The Pharmacological Basis of Therapeutics" Joel G. Hardman et al., eds., McGraw-Hill Professional, 13$^{th}$ edition. 2017, 1259584739); and "Handbook of Pharmaceutical Excipients" (Raymond C. Rowe et al., APhA Publications, 5$^{th}$ edition, 2005; 1582120587), each incorporated herein by reference in their entirety.

In another embodiment, wetting agents, emulsifiers and lubricants, such as sodium lauryl sulfate and magnesium stearate, as well as coloring agents, release agents, coating agents, sweetening, flavoring and perfuming agents, preservatives and antioxidants may also be present in the compositions described herein. Exemplary pharmaceutically acceptable antioxidants include, but are not limited to: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

In another embodiment, the pharmaceutically acceptable carrier or excipient is a binder. As used herein, "binders" refers to materials that hold the ingredients in a tablet together. Binders ensure that tablets and granules can be formed with the required mechanical strength, and give volume to low active dose tablets. Exemplary pharmaceutically acceptable binders include, but are not limited to: (1) saccharides and their derivatives, such as sucrose, lactose, starches, cellulose or modified cellulose such as microcrystalline cellulose, carboxy methyl cellulose, and cellulose ethers such as hydroxypropyl cellulose (HPC), and sugar alcohols such as xylitol, sorbitol or maltitol; (2) proteins such as gelatin; and (3) synthetic polymers including polyvinylpyrrolidone (PVP) and polyethylene glycol (PEG).

Binders can be classified according to their application. Solution binders are dissolved in a solvent (i.e. water or alcohol in wet granulation processes). Exemplary solution binders include, but are not limited to, gelatin, cellulose, cellulose derivatives, polyvinylpyrrolidone, starch, sucrose and polyethylene glycol. Dry binders are added to the powder blend, either after a wet granulation step, or as part of a direct powder compression (DC) formula. Exemplary dry binders include, but are not limited to, cellulose, methyl cellulose, polyvinylpyrrolidone and polyethylene glycol. In terms of the present disclosure, the pharmaceutically acceptable carrier or excipient may be a solution binder, a dry binder or mixtures thereof.

In some embodiments, the pharmaceutically acceptable carrier and/or excipient used herein may be an organic solvent, an inorganic salt, a surfactant, and/or a polymer.

Exemplary inorganic salts include, without limitation, calcium carbonate, calcium phosphate, disodium hydrogen phosphate, potassium hydrogen phosphate, sodium chloride, zinc oxide, zinc sulfate, and magnesium trisilicate.

Surfactants that may be present in the compositions of the present disclosure include zwitterionic (amphoteric) surfactants, e.g., phosphatidylcholine, and 3-[(3-cholamidopropyl) dimethylammonio]-1-propanesulfonate (CHAPS), anionic surfactants, e.g., sodium lauryl sulfate, sodium octane sulfonate, sodium decane sulfonate, and sodium dodecane sulfonate, non-ionic surfactants, e.g., sorbitan monolaurate, sorbitan monopalmitate, sorbitan trioleate, polysorbates such as polysorbate 20 (Tween 20), polysorbate 60 (Tween 60), and polysorbate 80 (Tween 80), cationic surfactants, e.g., decyltrimethylammonium bromide, dodecyltrimethylammonium bromide, tetradecyltrimethylammonium bromide, tetradecyltrimethyl-ammonium chloride, and dodecylammonium chloride, and combinations thereof.

Exemplary polymers include, without limitation, polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(amino acids), polyvinylpyrrolidone, polyethylene glycol, polyhydroxycellulose, chitin, chitosan, and copolymers, terpolymers, or combinations or mixtures thereof.

The composition may have <0.01, 0.01. 0.02, 0.05, 0.1, 0.2, 0.5, 1, 2, 5, 10, 20, 50, 100 or >100 µM of the gold(I) complex of formula (I) relative to the total volume of the composition.

A composition may contain <0.01, 0.01, 0.02, 0.05, 0.1, 0.2, 0.5, 1, 2, 5, 10, 20, 50 or >50 wt % of a gold(I) complex of formula (I) based on a total weight of the composition or any intermediately value within this range.

To reduce viability of cancer cells or abnormally proliferating cells, a subject may be treated with a concentration of a gold(I) complex described herein such as complex (1) or (2) ranging from 5, 10, 20, 30, 40, 50, 60, 70, 80, 90 or 100 µM or with an amount that contacts the cells in the subject to a concentration of 5, 10, 20, 30, 40, 50, 60, 70, 80, 90 or 100 µM of the gold(I) complex.

To reduce proliferation of cancer cells or abnormally proliferating cells, a subject may be treated with a concentration of a gold(I) complex, such as complex (1) or (2), described herein ranging from 1, 2, 5, 10, 20, 30, 40, 50, 60, 70, 80, 90 or 100 µM or with an amount that contacts the proliferating cells in the subject to a concentration of 1, 2, 5, 10, 20, 30, 40, 50, 60, 70, 80, 90 or 100 µM of the gold(I) complex. The ranges in the preceding paragraphs include all subranges and intermediate values. Preferably, a dosage of about 25, 30, 35, 40, 45, or 50 µM of a gold(I) complex of the invention is used.

The gold(I) complexes of the invention, such as gold complex (1), may be used to modulate or upregulate the expression of caspaces such as Caspase 3 and 9, and to induce apoptosis in target cells.

Depending on the route of administration e.g. oral, parental, or topical, the composition may be in the form of solid dosage form such as tablets, caplets, capsules, powders, and granules, semi-solid dosage form such as ointments, creams, lotions, gels, pastes, and suppositories, liquid dosage forms such as solutions, and dispersions, inhalation dosage form such as aerosols, and spray, or transdermal dosage form such as patches.

In other embodiments, the composition having the gold(I) complex of Formula (I) of, the salt thereof, the solvate thereof, the tautomer thereof may be prepared in a form for immediate release or sustained release.

The term "immediate release" refers to the release of a substantial amount of an active ingredient immediately upon administration. Typically, an immediate release indicates a complete (100%) or less than complete (e.g. about 70% or more, about 75% or more, about 80% or more, about 85% or more, about 90% or more, about 95% or more, about 99% or more, 99.9%, or 99.9%) dissolution of an active ingredient within 1-60 minutes, 1-30 minutes, or 1-15 minutes after administration.

The term "sustained release" refers to the release of an active ingredient from a composition and/or formulation over an extended period of time. In some embodiments, a sustained release indicates a dissolution of an active ingredient over a period of time up to 30 minutes, 60 minutes, 3 hours, 12 hours, 24 hours upon administration. In one embodiment, the compositions described herein do not have a sustained release.

Solid dosage forms for oral administration may include capsules, tablets, pills, powders, and granules. In such solid dosage forms, the active ingredients are ordinarily combined with one or more adjuvants appropriate to the indicated route of administration. If administered per os, the active ingredients can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled release formulation as can be provided in a dispersion of active compound in hydroxypropylmethyl cellulose. In the case of capsules, tablets, and pills, the dosage forms can also include buffering agents such as sodium citrate, magnesium or calcium carbonate or bicarbonate. Tablets and pills can additionally be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

The term "parenteral", as used herein, includes subcutaneous, intravenous, intramuscular, and intrasternal injection, or infusion techniques. For therapeutic purposes, formulations for parenteral administration can be in the form of aqueous or non-aqueous isotonic sterile injection solutions or suspensions. These solutions and suspensions can be prepared from sterile powders or granules having one or more of the pharmaceutically acceptable carriers or excipients mentioned for use in the formulations for oral administration. The active ingredients can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Injectable preparations, for example, sterile injectable aqueous or oleaginous suspensions, can be formulated according to the known art using suitable dispersing or wetting agents and suspending agents. The sterile injectable preparation may also be a sterile injectable solution or suspension in a pharmaceutically acceptable diluent or solvent. Among the pharmaceutically acceptable diluents and solvents that may be employed are water, Ringer's solution, and isotonic sodium chloride solution. In addition, sterile, fixed oils are conventionally employed as a solvent or suspending medium. For this purpose, any bland fixed oil may be employed, including synthetic mono- or diglycerides. In addition, fatty acids such as oleic acid are useful in the preparation of injectables. Dimethyl acetamide, surfactants including ionic and non-ionic detergents, and polyethylene glycols can be used. Mixtures of solvents and surfactants such as those discussed above are also useful.

Examples

As shown by the following Examples, water-soluble gold(I) complexes of the type [Au(Ipr)(L)]$PF_6$, where L=Tu (1) or $Me_2Tu$ (2) were synthesized from the parent [(Ipr) AuCl] (0). These complexes (0-2) were fully characterized by elemental analysis (EA), FT-IR, $^1H$, $^{13}C$, $^{77}Se$ NMR liquid state and $^{13}C$ solid state. Single crystal X-ray diffraction analysis shows that both complexes have a linear geometry. The in vitro cytotoxic activity of the complexes and cisplatin was investigated using an MTT assay against MG-63, HCT15, and HeLa cell lines. The $IC_{50}$ values showed that the complexes (1) and (2) exhibited a cytotoxicity higher than cisplatin against all cancer cell lines except complex (2) against HeLa. The interaction of complexes with amino acids were evaluated electrochemically in a phosphate buffer aqueous solution using cyclic voltammetry. Complex (1) interacted more with L-tryptophan than complex (2). The reduction in peak height and peak current was observed by the interaction of both complexes with L-tryptophan. The cell death mechanism was measured by studying the expression levels of Caspase-3 and Caspase-9 gene. The treatment of complex (1) with HCT-15 and HeLa cells resulted in the induction of apoptosis and a significant upregulation in the expression of both caspase-3 and 9, whereas, no significant deviation in the expression was noted in the complex (1) treated MG-63 cells.

Materials, Instruments and Methods.

All chemicals and solvents used in the synthesis were of analytical grade and used without further purification. [Au (Ipr)Cl], $AgPF_6$, thiourea, N,N'-dimethylthiourea, L-tryptophan, sodium phosphate mono basic and disodium phosphate were purchased from Sigma-Aldrich St. Louis, Mo. United States. $CH_2Cl_2$, methanol and ethanol were purchased from Strem Chemicals, Massachusetts, United States. For experiment and solution preparation, double distilled water was used. It was obtained from Lab based Water Still Aquatron A 4000 D unit.

Elemental analyses were performed on Perkin Elmer Series 11(CHNS/O), Analyzer2400. The solid state FTIR spectra of the ligands and their gold(I) complexes were recorded on a Perkin Elmer FTIR 180 spectrophotometer using KBr pellets over the range 4000-400 $cm^{-1}$ at resolution 4.0 $cm^{-1}$. Melting point analysis was carried out on Barnstead/Electrothermal (BI) 9100. $^1H$ and $^{13}C$ NMR spectra recorded on a LAMBDA Jeol 500 spectrophotometer operating at 500.01 and 125.65 MHz respectively; corresponding to a magnetic field of 11.74 T. Tetramethylsilane (TMS) was used as an internal standard for $^1H$ and $^{13}C$ NMR measurements. The $^{13}C$ NMR spectra obtained with $^1H$ broadband decoupling, and the spectral conditions were: 32 k data points, 0.967 s acquisition time, and 1.00 s pulse delay and 45° pulse angle. $^{13}C$ (MAS) NMR results recorded on a Bruker 400 MHz spectrometer at ambient temperature of 25° C. Samples were packed into 4 mm zirconium oxide rotors. Pulse delay of 7.0 s and a contact time of 5.0 ms. The magic angle spinning rates were 4 and 8 kHz. Carbon chemical shifts were measured relative to adamantane at 38.56 ppm.

Auto Lab (Netherland) was used as an electrochemical work station for the cyclic voltammetric experiment. The electrochemical experiment was performed using three electrode systems. Platinum as a counter, glassy carbon electrode as a working and Ag/AgCl was used as a reference electrode for all electrochemical measurements. The pH and the weight measurements of various chemicals were done using Accumet® XL50 pH meter and GR-2000 instruments, respectively.

Synthesis of Gold(I) Complexes.

The complexes were synthesized using a modification of a previously reported procedure; see M. Altaf et al. (2014), incorporated herein by reference in its entirety. $AgPF_6$ (0.127 g, 0.500 mmol) was dissolved in 5.0 mL ethanol and added to a solution of 1,3-Bis(2,6-di-isopropylphenyl)imidazol-2-ylidenechloridogold(I), [Au(Ipr)(Cl)] (0.311 g, 0.500 mmol) in 5.0 mL $CH_2Cl_2$. Then stirred for 5 min at room temperature and filtered off. Tu (0.038 g, 0.500 mmol) and $Me_2Tu$ (0.052 g, 0.500 mmol) were added to the filtrate, stirred for 1 hour and then filtered off. The synthesized complexes were kept in an undisturbed area. After three days, colorless crystals were obtained and a suitable crystal was chosen for X-ray diffraction analysis.

[Au(Ipr)(κ$SCN_2H_4$)]$PF_6$ (1). Yield 0.313 g, 75%. $C_{28}H_{40}Au$ $F_6N_4SP$. Calcd. C, 41.69, H, 4.99, N, 6.94, S, 3.97; found C, 40.04, H, 5.23, N, 6.04, S, 3.74. M. P. 243-246° C.

[Au(Ipr)(κ$SCN_2C_2H_8$)]$PF_6$ (2). Yield 0.245 g, 61%. $C_{30}H_{44}AuF_6N_4SP$. Calcd. C, 43.16, H, 5.31, N, 6.71, S, 3.84; found C, 42.26, H, 5.57, N, 7.20, S, 3.66. M.P. 183-186° C.

In some embodiments alternative ingredients, such as $AgNO_3$ instead of $AgPF_6$, solvents such as $H_2O$ or $CHCl_3$, and a temperature range of 20-27° C. may be used. Some alternative preparation steps include adding Tu (0.038 g, 0.500 mmol) and $Me_2Tu$ (0.052 g, 0.500 mmol) to a solution of 1,3-Bis(2,6-di-isopropylphenyl)imidazol-2-ylidenechloridogold(I), [Au(Ipr)(Cl)] (0.311 g, 0.500 mmol) in 5.0 mL $CH_2Cl_2$ or $CHCl_3$ and stirred for 2 hours.

Gold (I) complexes of Formula (I) are produced using Tu (thiourea) substituted with hydrogen, $C_{1-6}$ alkyl, $C_{2-6}$ alkenyl, $C_{2-6}$ alkynyl, or $C_{4-10}$ aryl. For example, complex (1) and complex (2) as described herein are respectively produced using thiourea, which has two hydrogen substituents at R1 and R2, and thiourea substituted with methyl at R1 and R2 (dimethylthiourea).

Single Crystal Structure Determination.

Suitable Crystals of complexes (1) and (2) were obtained as colorless plats from dichloromethane/ethanol. The X-ray data were collected at 173K (-100° C.) on a STOE IPSD II Image Plate Diffraction System connected with a two-circle goniometer and using a MoKα graphite monochromator (λ=0.71073 Å); see G. Stoe & Cie, X-Area & X-RED32. Stoe & Cie GmbH, Darmstadt, 2009 Germany, incorporated herein by reference in its entirety. The structure was solved by a SHELXS-2014 program; see G. M. Sheldrick, Acta Cryst., 2008, A64, 112-122, incorporated herein by reference in its entirety. The refinement and further calculations were carried out with a SHELXL-2014.

The NH H atoms were located in a difference Fourier map and refined with a distance restraint of N—H=0.88(2) A and H . . . H=1.40(2) Å. The C-bound H-atoms were included in the calculated positions and treated as riding atoms: C—H=0.95-1.0 Å with $U_{iso}(H)$=1.5 $U_{eq}(C)$ for methyl H atoms and =1.2 $U_{eq}(C)$ for other H-atoms. The non-H atoms were refined anisotropically, using weighted full-matrix least-squares on $F^2$. A semi-empirical absorption correction was applied using the MULscanABS routine in PLATON; see A. L. Spek, Acta Cryst., 2009, D65, 148-155; and C. F. Macrae, I. J. Bruno, J. A. Chisholm, P. R. Edgington, P. McCabe, E. Pidcock, L. Rodriguez-Monge, R. Taylor, J. Van de Streek, P. A. Wood, *J. Appl. Cryst.* 2008, 41, 466-470, each incorporated herein by reference in their entirety. The F atoms of the $PF_6^-$ anion are disordered. The best solution was found by distributing the electron density over a total of 11 positions, which were refined with various fixed occupancy ratios to give a total of six F atoms. The symmetry of the crystal data and structure refinement is demonstrated in Table 6.

MTT Assay for In Vitro Cytotoxicity of Gold(I) Complexes.

Gold(I) complexes (0-2) and cisplatin were tested for their in vitro cytotoxic effects against the MG-63, HCT15 and HeLa cell lines; M. Altaf, M. Monim-ul-Mehboob, A. A. Isab, V. Dhuna, G. Bhatia, K. Dhuna, "The synthesis, spectroscopic characterization and anticancer activity of new mono and binuclear phosphanegold(I) dithiocarbamate complexes," *New J. Chem.*, 2015, 39, 377-385, incorporated herein by reference in its entirety.

The cells were seeded at $3 \times 10^3$ cells/well in 100 µL of DMEM containing 10% fetal bovine serum (FBS) in a 96-well tissue culture plate and incubated for 72 h at 37° C., 5% $CO_2$ and 90% relative humidity in a $CO_2$ incubator. After incubation, 100 µL of (25, 12.5, 6.25 and 3.75 µM) solutions of cisplatin, gold(I) complexes (0-2) prepared in DMEM were added to the cells, and then the cultures were incubated for 72 h. The medium in the wells was casted off and 100 µL of DMEM containing MTT (0.5 mg/ml) was added to the wells, with subsequent incubation in the $CO_2$ incubator at 37° C. in the dark for 4 h. After incubation, purple-colored formazan produced by the cells appeared as dark crystals in the bottom of the wells. The culture medium was carefully removed from each well to prevent disruption of the monolayer and 100 µL of dimethyl sulfoxide (DMSO) was added to each well. The solution in the wells was thoroughly mixed to dissolve the formazan crystals which produced a purple solution. The absorbance of the 96 well-plates was measured at 570 nm with a LabSystems Multiskan EX ELISA reader against a reagent blank. The experimental results were calculated as a micro-molar concentration of 50% cell growth inhibition ($IC_{50}$) of each drug. An MTT assay was carried out in three independent experiments, each in triplicate.

Electrochemical Measurements.

The electrochemical measurements were done using a glassy carbon electrode. For electrochemical analysis, a GCE surface was polished by rubbing on the synthetic cloth containing alumina slurry. The GCE surface was polished before every electrochemical measurement. Interaction of the complexes was considered with biomolecules using cyclic voltammetry. The cyclic voltammetry was scanned from 0.0 to 1.2 or −0.4 to 1.2 V.

Semi-Quantitative Reverse Transcription Polymerase Chain Reaction.

The underlying molecular mechanism for the anti-cancer activity of different gold complexes was determined. The gene expression of caspase family proteins i.e. caspase 3 (CASP3) and caspase 9 (CASP9) was examined by constructing a first transcript (cDNA) from their respective mRNA by reverse transcription. Further, the cDNA was amplified and electrophoresed on 2% agarose gel. β-actin (ACTB) was used as an internal control. The primer pairs for the desired genes were custom-synthesized from Bioserve Biotechnologies (Hyderabad, India) as shown in Table 1.

TABLE 1

Primers sequence used for semi-quantitative RT-PCR

| Sr. no. | mRNA | Primers | Sequence (5'→3') | PCR Product |
|---|---|---|---|---|
| 1 | CASP9 | Forward | ATGATCGAGGACATCCAGCG (SEQ ID NO: 1) | 266 bp |
| | | Reverse | CTGGGTGTTTCCGGTCTGAG (SEQ ID NO: 2) | |
| 2 | CASP3 | Forward | CTCGGTCTGGTACAGATGTCG (SEQ ID NO: 3) | 263 bp |
| | | Reverse | ACTTCTACAACGATCCCCTCTG (SEQ ID NO: 4) | |
| 3 | ACTB | Forward | TCACCCACACTGTGCCCATCTACGA (SEQ ID NO: 5) | |
| | | Reverse | CAGCGGAACCGCTCATTGCCAATGG (SEQ ID NO: 6) | 295 bp |

IR Spectroscopy.

The IR frequency bands at 842 and 985 $cm^{-1}$ were assigned to the C=S stretching vibration of 1 and 2, which is significantly shifted to a lower frequency with respect to their position in free Tu and $Me_2Tu$ (1040 and 1080 $cm^{-1}$). The shift indicates a decrease in the double bond character of C=S due to the mesomeric effect of the neighboring nitrogen atoms. The N—H stretching shows a significant shift to a higher frequency (3471, 3369; 3377 Vs 3405, 3274; 3267 $cm^{-1}$). See D. N. Sathyanarayana, "Vibrational Spectroscopy: Theory and Applications," *New Age Intl. Publishers*, 1st Edition, 2004; K. Aktiviti, A. Kompleks, C. Li, "Synthesis, characterisation and antibacterial studies of Cu(II) complexes thiourea," *malaysain J. Anal. Sci.*, 2012, 16(1), 56-61; J. T. J. Prakash, L. R. Nirmala, "Synthesis, spectral and thermal properties of bis thiourea zinc Acetate (BTZA) single crystals," *intl. J. Comput. Appl.*, 2010, 6(7) 7-11; and U. Anthoni, G. Borch, P. Klaboe, P. H. Nielsen, "Tentative assignments of fundamental vibrations of thio- and selenoamides. VIII. 1,2-Dimethyl-3-pyrazolidineselone, a cyclic selenohydrizide. selenation of the thioamide group in theory and practice," *Acta Chem. Scand. A*, 1982, 36, 69-77, each incorporated herein by reference in their entirety. The C=S group forms a considerably stronger bond than that of C=Se. See P. J. Hendra, Z. Jović "The laser Raman and infra-red spectra of some thiourea and selenourea complexes of platinum(II) and palladium(II)," *Spectrochim. Acta*, 1968, 24, 1713-1720; H. Rostkowska, L. Lapinski, A. Khvorostov, M. J. Nowak, "Proton transfer processes in selenourea: UV-induced selenone→selenol photoreaction and ground state selenol→selenone proton tunneling," *chem. phys.*, 2004, 298, 223-232; and N. N. Golovnev, A. A. Leshok, G. V. Novikova, A. I. Petrov "Stability of Bismuth(III), Indium(III), Lead(II), and Cadmium(II) monocomplexes with selenourea and thiourea," *Russ. J. Inorg. Chem.*, 2010, 55, 130-132, each incorporated herein by reference in their entirety. Weak signals at 2960 & 3073 $cm^{-1}$ for [Au(IPr)Cl] and 2869, 2963; 2873, 2931 & 3162, 3166 $cm^{-1}$ for 1 and 2 due to C—H stretching vibrations of IPr were also observed. The IR data for free ligands and complexes is shown in Table 2.

TABLE 2

Mid FT-IR frequencies (cm$^{-1}$) of free ligand and Au(I) complexes (0-2)

| Ligand/Complex | Stretch NH | | | | | | | Stretch C=S |
|---|---|---|---|---|---|---|---|---|
| [Au(Ipr)Cl] | — | 3073 | 1109 | 2960 | 1366 | 1258 | 1462 | — |
| Tu | 3405, 3274 | — | — | — | — | 1616 | 1468 | 1080 |
| 1 | 3471, 3369 | 3166 | 1059 | 2963, 2869 | 1466 | 1630 | 1466 | 842 |
| Me$_2$Tu | 3267 | — | — | — | 1444 | 1525 | — | 1040 |
| 2 | 3377 | 3162 | 1133 | 2931, 2873 | 1371 | 1571 | 1462 | 985 |

NMR Spectroscopy.

The $^1$H and $^{13}$C NMR chemical shifts of ligands and their complexes are given in Tables 2 and 3. The $^1$H chemical shifts associated with the IPr part of 1 and 2 were observed in the same region as the [Au(IPr)Cl] reported in the literature [41, 40], while the N—H resonance of Tu and Me$_2$Tu in 1 and 2 (7.28 and 8.16 ppm) shifted downfield by about 1.5 ppm compared to their values in the free ligands.

TABLE 3

$^1$H NMR chemical shifts (ppm) for free ligand and gold(I) complexes (0-2) in CDCl$_3$

| Ligand/complex | H-3 | H-4 | H-5 | H-6 | H-7 | H-8 | H-9 | N—H |
|---|---|---|---|---|---|---|---|---|
| [Au(Ipr)Cl] (0) | 7.39 d | 7.55 t | 2.46 m | 1.33 d | 1.21 d | 7.98 s | — | — |
| 1 | 7.36 d | 7.62 t | 2.49 m | 1.30 d | 1.24 d | 6.91 s | — | 7.28 |
| 2 | 7.35 d | 7.52 t | 2.50 m | 1.26 d | 1.21 d | 7.84 s | 2.80 s | 8.16 |
| Tu | — | — | — | — | — | — | — | 6.81 |
| Me$_2$Tu | — | — | — | — | — | — | 2.81 s | 6.62 |

A $^{13}$C NMR chemical shift of the Au=C resonance in the [Au(Ipr)Cl] was observed at 175.3 ppm and it was shifted downfield by ≈6.0 ppm in 1 and 2 at 180.3 and 181.1 ppm, respectively. The downfield shift was related to a back donation from the d-orbital of the Au atom to π* C=S and the transferred electron density of N→C resulting in a partial double character in the C—N bond which confirms that the coordination is done through binding to the sulfur atom; see A. S. Vinogradov, A. B. Preobrajenski, A. Knop-Gericke, S. L. Molodtsov, S. A. Krasnikov, S. V. Nekipelov, R. Szargan, M. Hävecker, R. Schlogl, "Observation of back-donation in 3d metal cyanide complexes through N K absorption spectra," *J. Electron Spectrosc. Relat. Phenomena.*, 2001, 116, 813-818, incorporated herein by reference in its entirety.

The other resonances of the IPr ligand remained almost unchanged. However, the C=S resonance in 1 and 2 shifted up-field by 6.0 and 10 ppm with respect to its position in the free ligands as reported in the literature; see A. A. Isab, S. Ahmad, "Complexation of (trimethylphosphine)gold(I) with selenones," *Trans. Met. Chem.*, 2006, 31, 500-503, incorporated herein by reference in its entirety.

TABLE 4

$^{13}$C NMR chemical shifts (ppm) for free ligands and gold(I) complexes (0-2) in CDCl$_3$

| Ligand/complex | C1 | C2 | C3 | C4 | C5 | C6 | C7 | C8 | Au=C | C=S | C11 |
|---|---|---|---|---|---|---|---|---|---|---|---|
| [Au(Ipr)Cl](0) | 145.5 | 133.9 | 123.0 | 130.7 | 28.8 | 24.5 | 24.0 | 124.2 | 175.3 | — | — |
| 1 | 145.3 | 133.1 | 123.7 | 129.8 | 28.1 | 23.8 | 23.3 | — | 180.7 | 177.0 | — |
| 2 | 145.9 | 133.3 | 124.0 | 131.1 | 28.8 | 24.5 | 23.9 | 124.4 | 181.1 | 176.4 | 32.3 |
| Tu | — | — | — | — | — | — | — | — | — | 185.5 | — |
| Me$_2$Tu | — | — | — | — | — | — | — | — | — | 182.3 | 30.8 |

Figure 2:
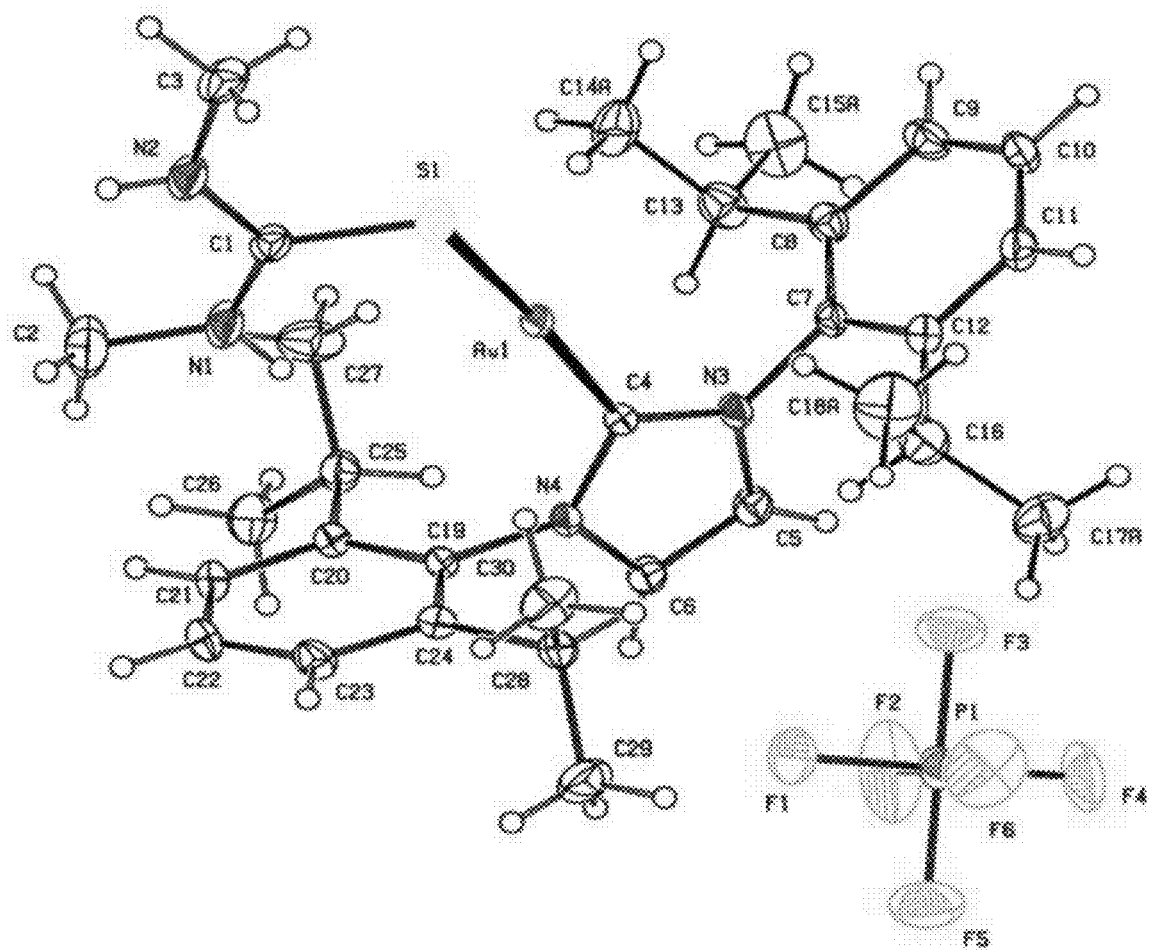
FIG. 2. Molecular structure of complex [Au(Ipr) (κSCN$_2$C$_2$H$_8$)PF$_6$ (2), with labelling atoms and 50% probability ellipsoids level.
Figure 3:
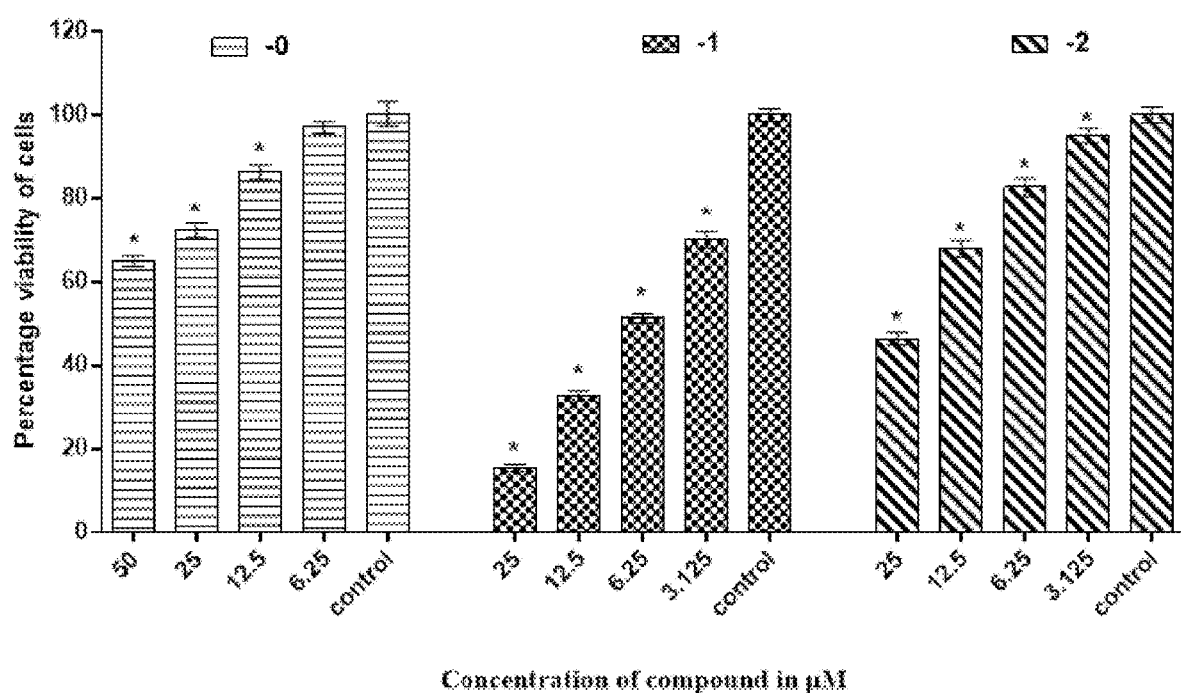
FIG. 3. Graph of cytotoxic effect of series complexes (0-2) concentrations on cell viability of HCT15 cell line.
Figure 4:
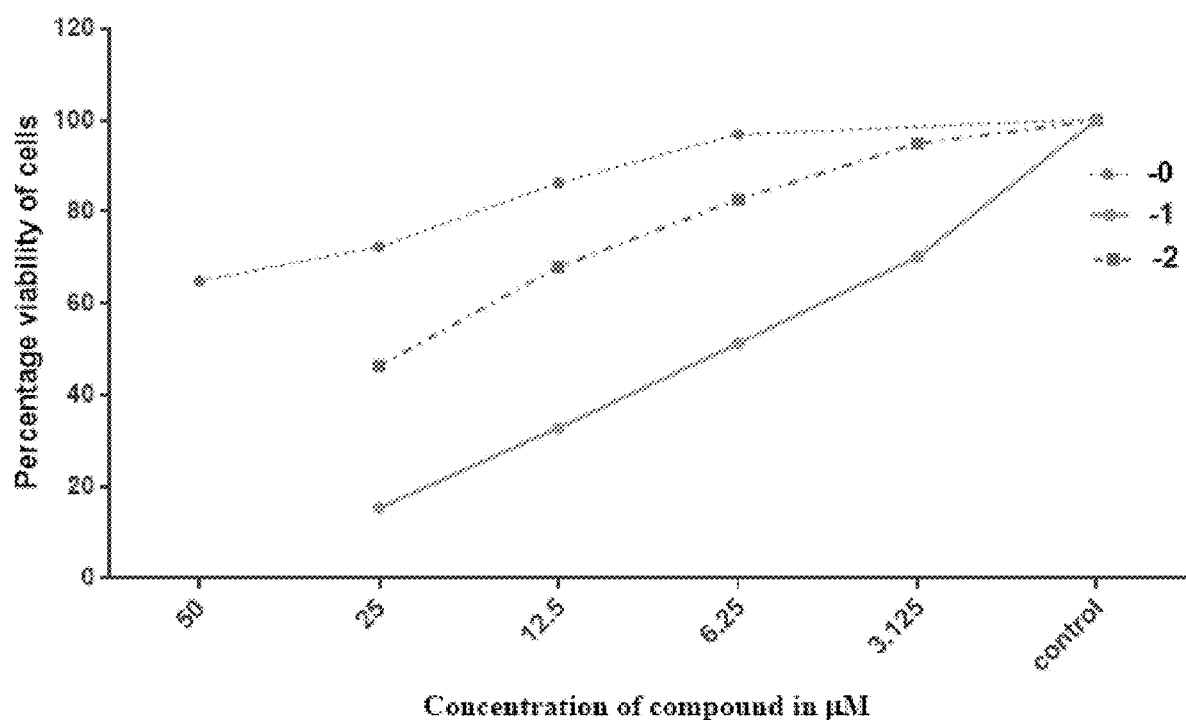
FIG. 4. In vitro cytotoxic effect of series complexes (0-2) concentrations on cell viability of HCT15 cell line.

Single crystal X-ray structure of complexes (1 and 2). The molecular structure of complexes [Au(IPr)(κSCN$_2$H$_4$]PF$_6$ (1) [Au(IPr)(κSCN$_2$C$_2$H$_8$]PF$_6$ (2) are shown in FIGS. 1 and 2. Selected bond lengths and angles are illustrated in Table 5. The geometry of the coordination around gold ion is close to linearity, with (C—Au—S) angle of 177.12(12) and 176.40(7°) respectively. The Au—C and C—S bond lengths are 2.2977(7); 1.724(3); 1.995 (4)Å; 1.706 (6), respectively. The bond lengths and bond angles are similar to those reported for analogous compounds. See 0. E. Piro, R. C. Piatti, A. E. Bolzan, R. C. Salvarezza, "X-ray diffraction study of copper(I) thiourea complexes formed in sulfate-containing acid solutions," *Acta Crystallogr.* B, 2000, 56, 993-7; M. Fettouhi, M. I. M. Wazeer, A. A. Isab, "Crystal structure of dibromo-bis(1,3-imidazolidine-2-thione-S)zinc (II)," *z. Krist. NCS,* 2006, 221, 221-222; M. Fettouhi, A. Isab, M. Wazeer, "Crystal structure of bis (3,4,5,6-tetrahy-dropyrimidine-2(1H)-thione-S)gold(I) chloride, [Au (C$_4$H$_8$N$_2$S)$_2$]Cl," *z. Krist. NCS,* 2004, 219, 2004; and F. Caddeo, V. Fernández-moreira, M. Arca, A. Laguna, V. Lippolis, M. C. Gimeno, "Gold thione complexes," *inorganics,* 2014, 2, 424-432, each incorporated herein by reference in their entirety. There is no Au—Au bond in both complexes.

TABLE 5

Selected bond lengths and bond angles for complexes (1) and 2

| Bond Length (Å) | | Bond Angles (°) | |
|---|---|---|---|
| Complex (1) | | | |
| Au1—S1 | 2.3024(13) | C1—Au1—S1 | 177.12 (12) |
| Au1—C1 | 1.995 (4) | C28—S1—Au1 | 103.6 (2) |
| S1—C28 | 1.706 (6) | N3—C28—N4 | 118.6 (6) |
| N3—C28 | 1.320 (9) | S1—C28—N3 | 123.0 (4) |
| N4—C28 | 1.321 (7) | S1—C28—N4 | 118.40 (4) |
| Complex (2) | | | |
| Au1—S1 | 2.2977(7) | C4—Au1—S1 | 176.40 (7) |
| Au1—C4 | 2.007 (2) | Au1—S1—C1 | 105.79 (10) |
| S1—C1 | 1.724 (3) | N1—C1—N2 | 119.20 (3) |
| N1—C1 | 1.326 (4) | S1—C1—N1 | 122.40 (2) |
| N2—C1 | 1.322 (4) | S1—C1—N2 | 118.40 (2) |

TABLE 6

Summary of crystal data and details of the structure refinement for complex (1) and 2

| Complex | 1 | 2 |
|---|---|---|
| Empirical formula | C$_{28}$H$_{40}$AuF$_6$N$_4$PS | C$_{30}$H$_{44}$AuF$_6$N$_4$PS |
| Formula weight | 806.63 | 834.69 |
| Crystal symmetry | Monoclinic | Monoclinic |
| Space group | P 21/n | P 21/c |
| Crystal color | | Colorless |
| Crystal size/mm | 0.65 × 0.39 × 0.20 | 0.40 × 0.32 × 0.20 |
| Wavelength/Å | 0.71073 | 0.71073 |
| Temperature/K. | 110 | 173 |
| a (Å) | 9.2495(8) | 8.6566 (2) |
| b (Å) | 15.474(14) | 23.5651 (9) |
| c (Å) | 23.370(2) | 17.3653 (5) |
| α (°) | 90.0 | 100.394 (5) |
| β (°) | 96.419(2) | 98.966 (2) |
| γ (°) | 90.0 | 95.727 (5) |
| Cell volume (Å$^3$) | 3324.0(5) | 3499.12 (19) |
| D$_x$ (g m$^{-3}$) | 1.612 | 1.686 |
| μ (mm$^{-1}$) | 4.594 | 4.37 |
| Radiation type | Mo Kα | Mo Kα |
| Z | 4 | 4 |
| Diffractometer | Bruker Smart Apex area detector | STOE IPDS 2 |
| Absorption correction | Multi-scan SADABS; Sheldrick, 1996 | Multi-scan (MULABS in PLATON, (2009) |
| Radiation source | | Plane graphite |
| R[F$^2$ > 2σ(F$^2$)], wR(F$^2$), S | 0.051, 0.160, 1.07 | 0.020, 0.047, 1.01 |
| Δρ$_{max}$ (e Å$^{-3}$) | 2.09 | 0.90 |
| Δρ$_{min}$ (e Å$^{-3}$) | -3.31 | -0.58 |
| H-atom treatment: | | Treated by a mixture of independent and constrained refinement |

In Vitro Cytotoxic Activities of Gold(I) Complexes.

Gold(I) complexes (0-2) were tested for in vitro cytotoxicity against HeLa (human cervical cancer), MG-63 (human osteosarcoma (human bone cancer)), and HCT15 (human colon cancer) cancer cell lines using an MTT assay and compared with cisplatin (a standard anticancer drug). The respective IC$_{50}$ values (μM) of the gold(I) complexes (0-2) and cisplatin against cancer cell lines are shown in Table 7.

The results showed a significant reduction in cell viability with a subsequent increase in the concentration of gold complexes and cisplatin (p<0.005). However, the gold complexes in comparison to cisplatin were found to be highly cytotoxic at concentrations 100 and 50 μM. To calculate the IC50 value for the different complexes, the tested concentrations were reduced to 25 μM and to 3.12 μM (FIGS. 3-6). The IC$_{50}$ values were obtained from the curve of the concentration of cisplatin, and the complexes (0-2) against the percentage of cell viability.

Complex (1) has both better and lowered IC$_{50}$ values, and was therefore selected for the analysis of the underlying molecular mechanism of cytotoxicity. The data shows that complex (1) is the most active at inhibiting all cell cancer proliferation. Its antiproliferative activity against HCT15 (6.64 μM), MG-63 (1.76 μM), and HeLa (9.20 μM) was 2 to 17-fold better than cisplatin (30.2, 33.58, 20.55 μM) respectively.

The inhibition of cell proliferation and the higher cytotoxic effect of the complexes suggest that the S containing ligand is more labile and that it prevents the complexes from reacting with the thiol group of proteins and enzymes, such as albumin, which enhance the cytotoxic activity of the complexes.

TABLE 7

IC$_{50}$ values (μM) of cisplatin and gold(I) complex (1) and 2 against HCT15, A549 and MCF7 cancer cell lines

| Complex | HCT15 | MG-63 | HeLa |
|---|---|---|---|
| Cisplatin | 31.94 ± 0.55 | 33.37 ± 1.2 | 21.59 ± 0.73 |
| 0 | 119.82 ± 10.6 | 61.59 ± 3.65 | 171.56 ± 11.98 |
| 1 | 6.61 ± 0.18 | 1.76 ± 0.16 | 9.17 ± 0.18 |
| 2 | 23.89 ± 1.21 | 14.7 ± 1 | 42.66 ± 5.94 |

Interactions of the Complexes with Amino Acids.

Figure 9A:
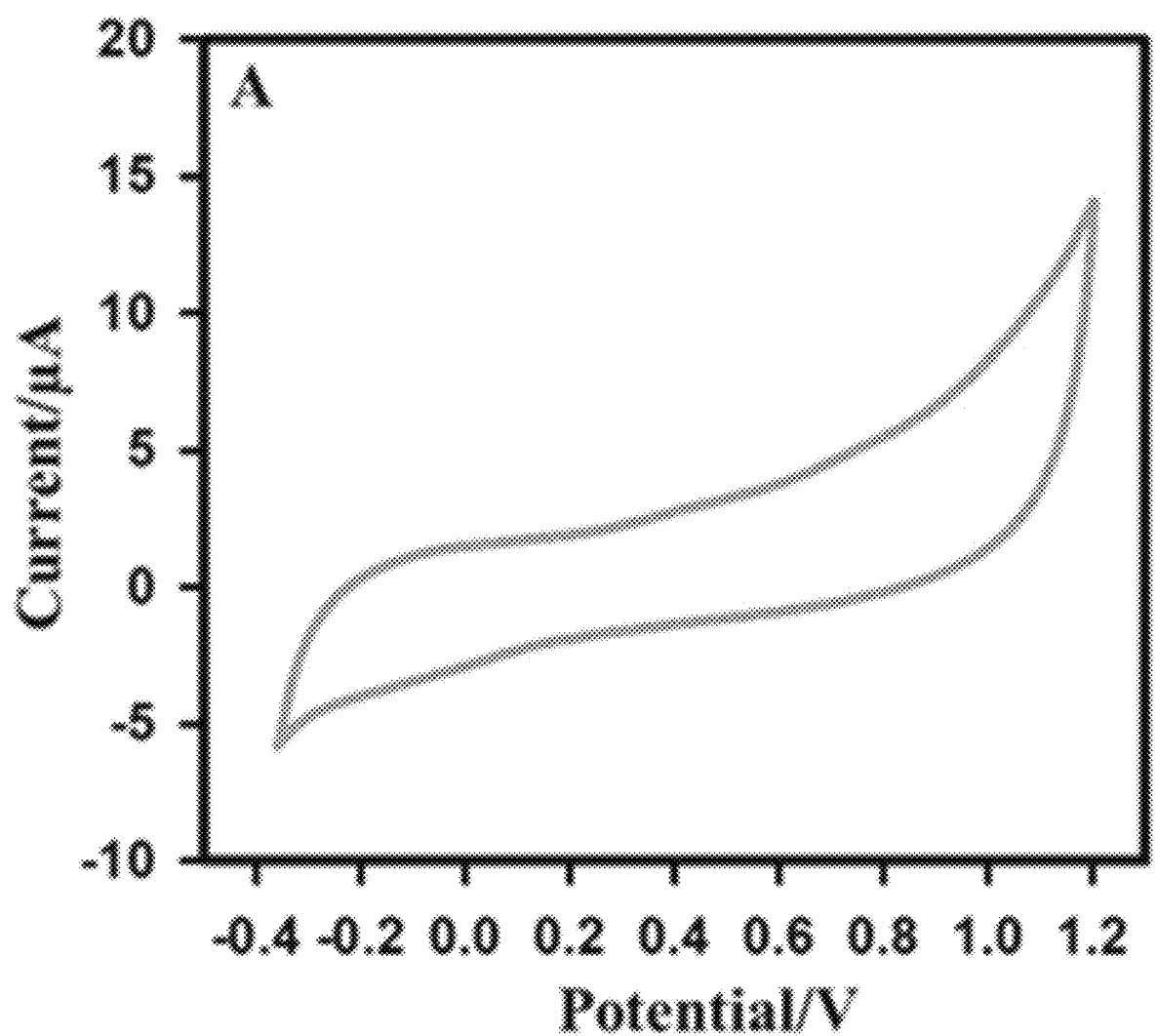
FIG. 9A. Cyclic voltammogram of the 0.1 mM complex (1) (A) in 0.1 M PB (pH 6.86).
Figure 9B:
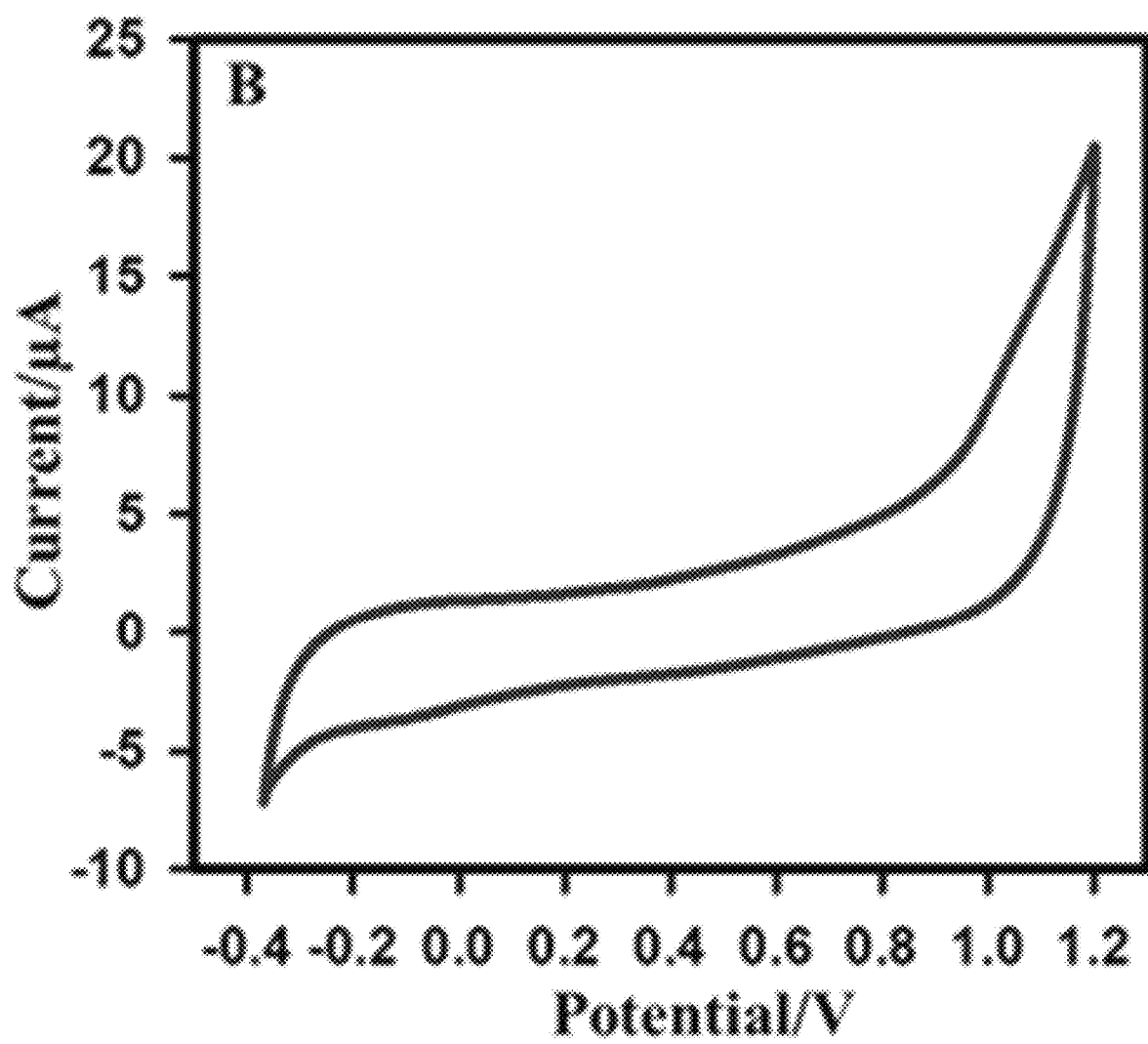
FIG. 9B. Cyclic voltammogram of the 0.1 mM complex (2) (B) in 0.1 M PB (pH 6.86).

Complexes (1) or (2) were evaluated electrochemically to observe their interactions with biomolecules. The complexes exhibited good solubility in water. The electrochemical behavior of the complexes was investigated using cyclic voltammetry. For this purpose, 0.1 mM complexes of 1 and 2 were scanned from -0.4 to 1.2 (FIG. 9). The complexes were found to be electrochemically stable and no peaks were observed in the scanned window. The electrochemical inactivity of the complexes restricted the examination of its interaction with electrochemically inactive biomolecules or proteins. To investigate the interaction of the complexes with biomolecules, the electroactive one was selected. Few amino acids, such as L-tyrosine, and the tryptophan, are electroactive amino acids; see M. Fettouhi (2006); and N. Baig, A-N Kawde, "A novel, fast and cost effective graphene-modified graphite pencil electrode for trace quantification of L-tyrosine", *Anal. Methods.*, 2015, 7, 9535-9541, each incorporated herein by reference in their entirety. The interaction of complex (1) and (2) was explored with tryptophan.

Figure 10A:
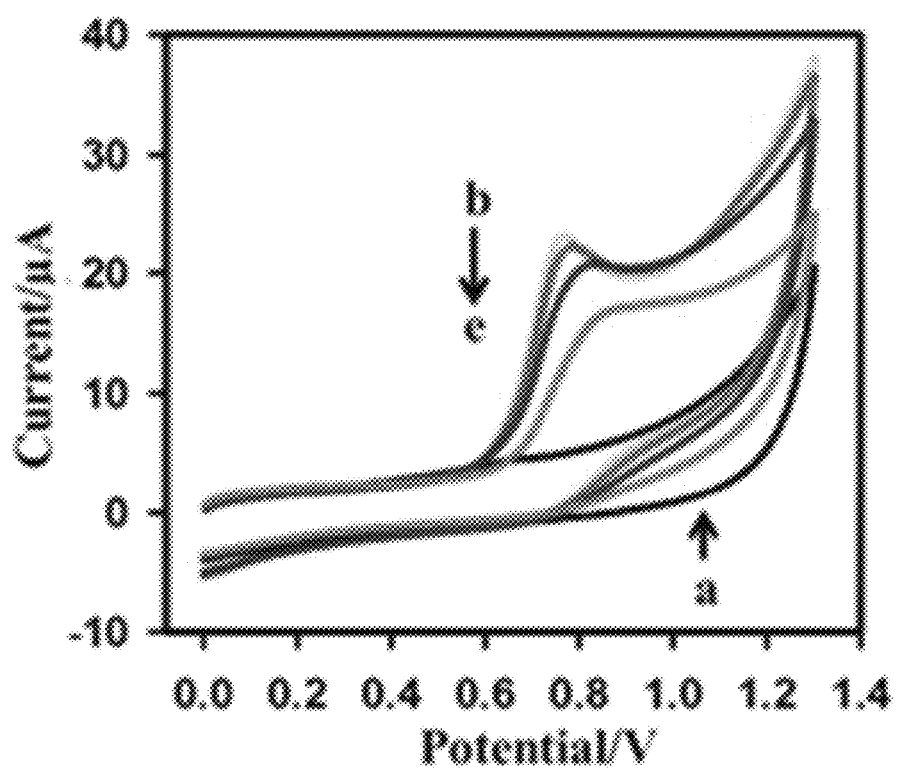
FIGS. 10A-10C. Cyclic voltammograms of the interactions of the complex (1) (FIG. 10A) and complex (2) (FIG. 10B) with 0.5 mM tryptophan in 0.1 M PB (pH 6.86) at different concentrations of complexes (1) and 2 (a) blank, absence of complex and tryptophan, (b) 0 μM (c) 10 μM, (d) 20 μM, (e) 40 μM. The response of 0.5 mM tryptophan solution in controlled experiment (FIG. 10C) by adding solvent blank (b) 0 (c) 15 (d) 30 μL, (e) 60 μL.
Figure 10B:
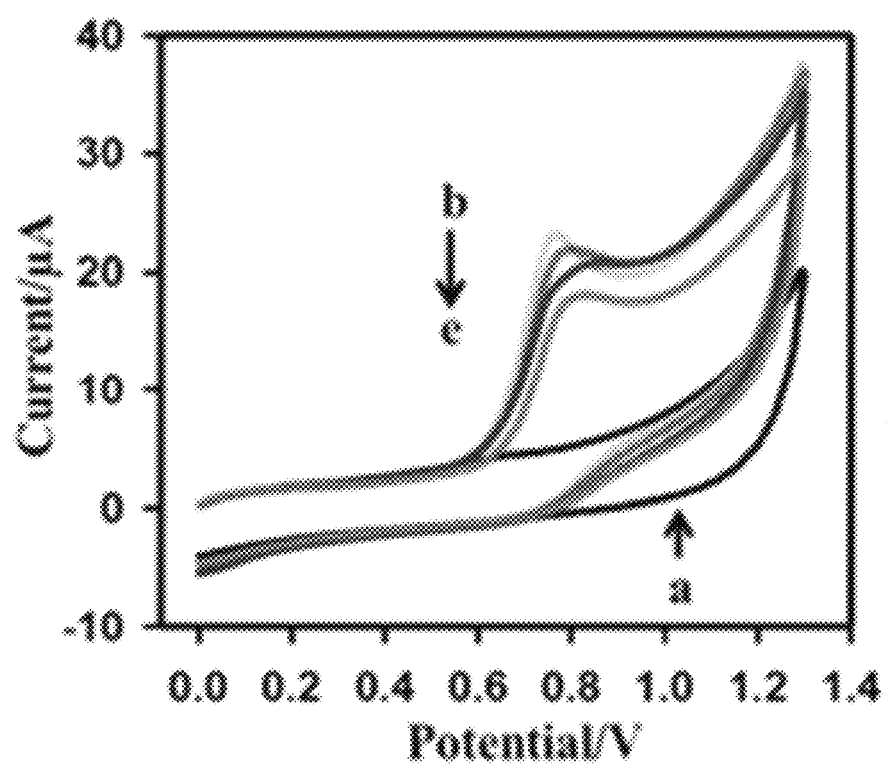
Figure 10C:
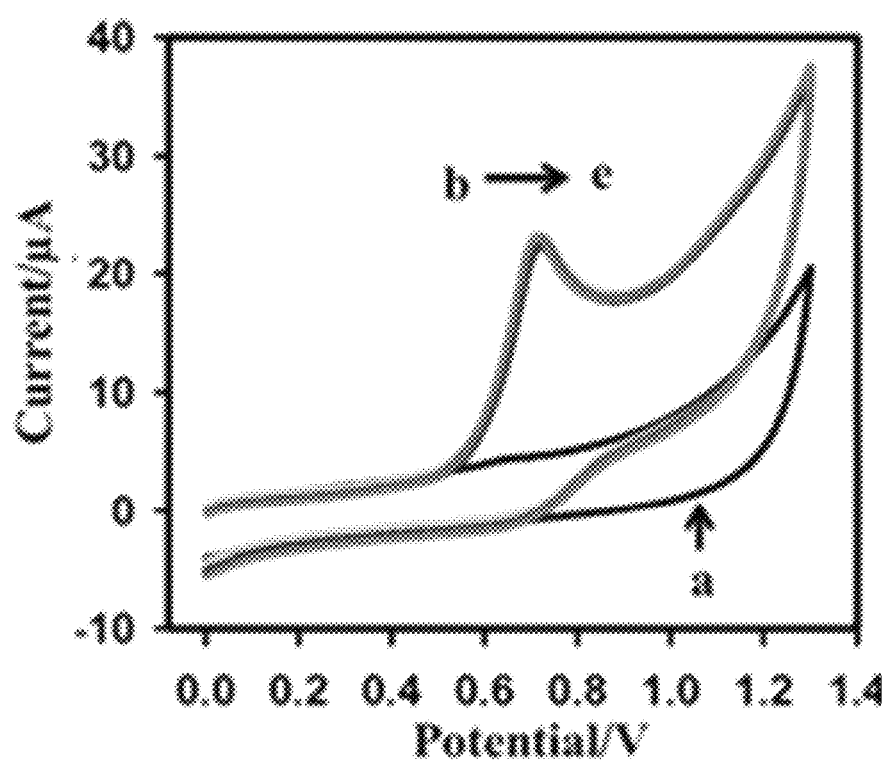

The interaction of the synthesized complexes with tryptophan was evaluated by spiking various concentrations of complexes (1) and (2) into 0.5 mM of tryptophan. The tryptophan peak appeared in a 0.1 M phosphate buffer at 0.758 V in the absence of the complexes. In FIG. 10A, the interaction of complex (1) could be seen with tryptophan. A significant decrease in the peak current was observed. A similar behavior was observed with the complex (2) (FIG. 10B). The spiking of various concentrations of complex (2) shows an obvious change in the peak shift and peak current. The peak of tryptophan was shifted from 0.758 to 0.803 V by spiking 40 µM of complexes (1) and (2). However, complex (1) demonstrated more effect on the peak shift and the peak current of the tryptophan. The peak of tryptophan was shifted to 0.850 V. The possible interaction is due to the presence of the amino group in the complexes which may interact through forming some sort of intermolecular forces. To eliminate the possible effect of the solvent, the equivalent volume of the solvent blank was added into the 0.5 mM tryptophan. In a controlled experiment, no effect on the peak shift and the current was observed as the spiked solvent blank maximum added volume is very small (FIG. 10C). It was observed that the change in the peak shift and the peak current is due to the interactions of the spiked complexes (1) and (2). The electrochemical study revealed that both complexes have a good capability to interact with amino acids and proteins.

Semi-Quantitative Reverse Transcription Polymerase Chain Reaction.

Figure 5:
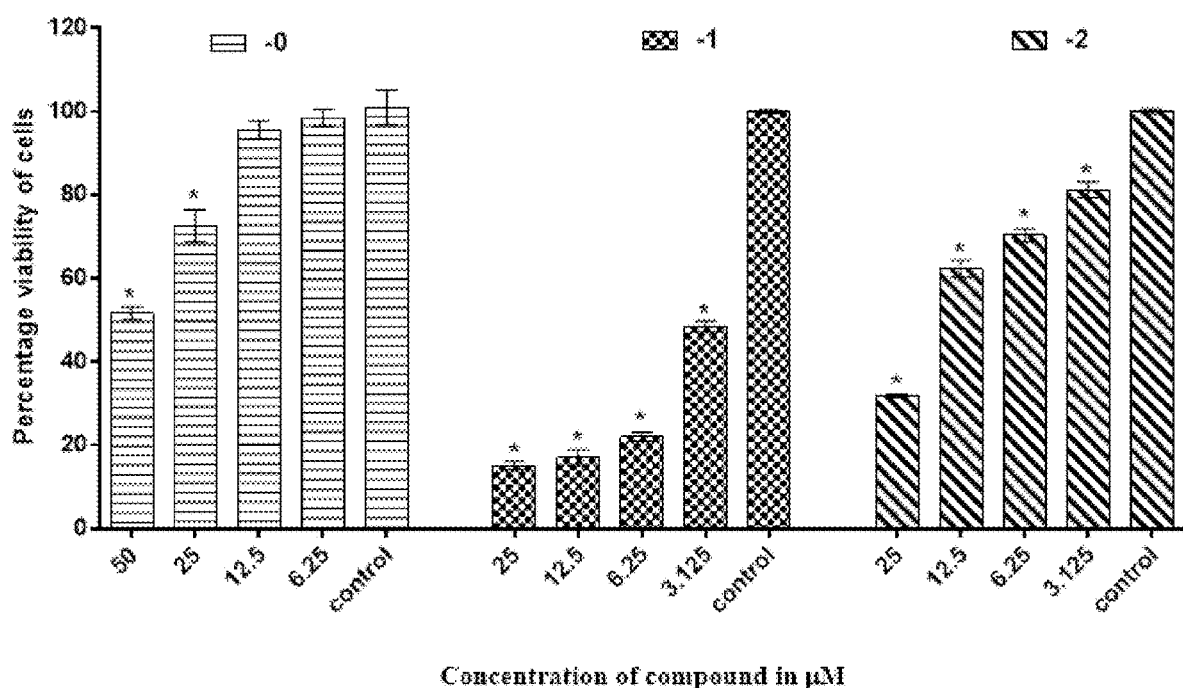
FIG. 5. Graph of cytotoxic effect of series complexes (0-2) concentrations on cell viability of MG-63 cell line.
Figure 6:
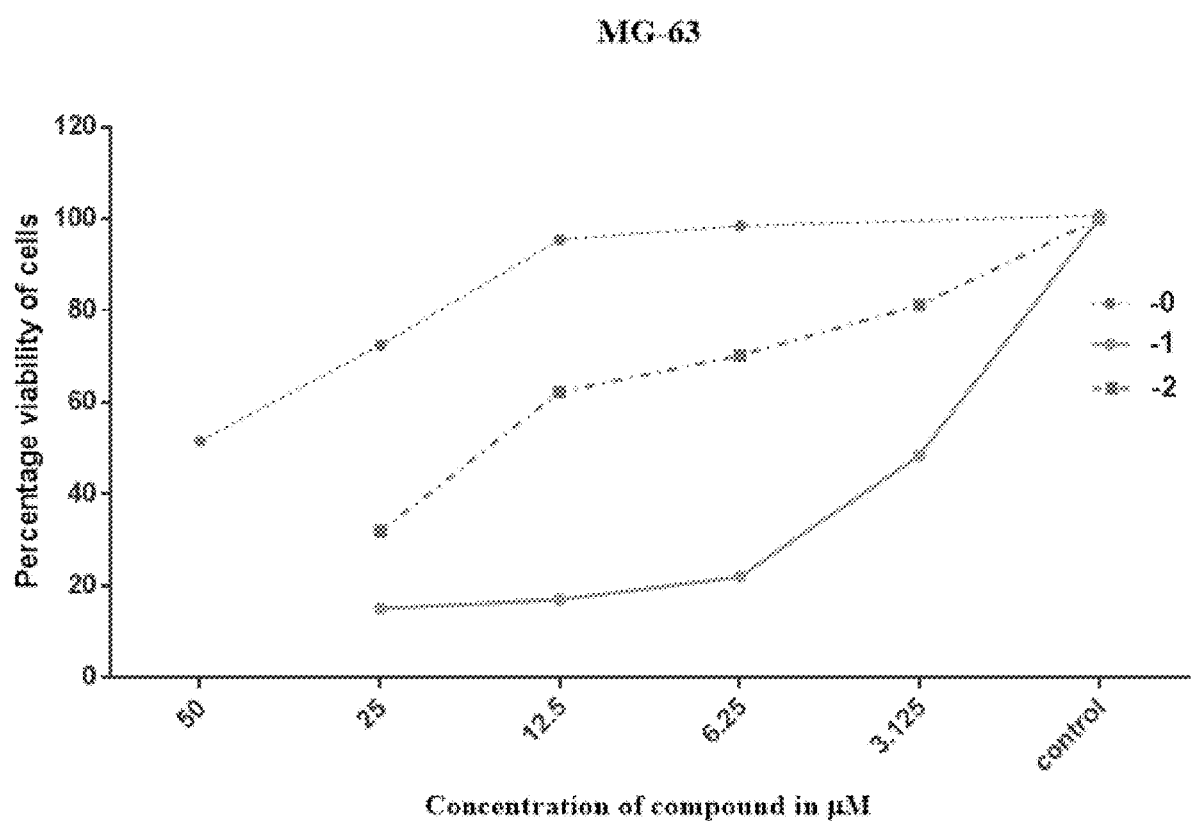
FIG. 6. In vitro cytotoxic effect of series complexes (0-2) concentrations on cell viability of MG-63 cell line.
Figure 7:
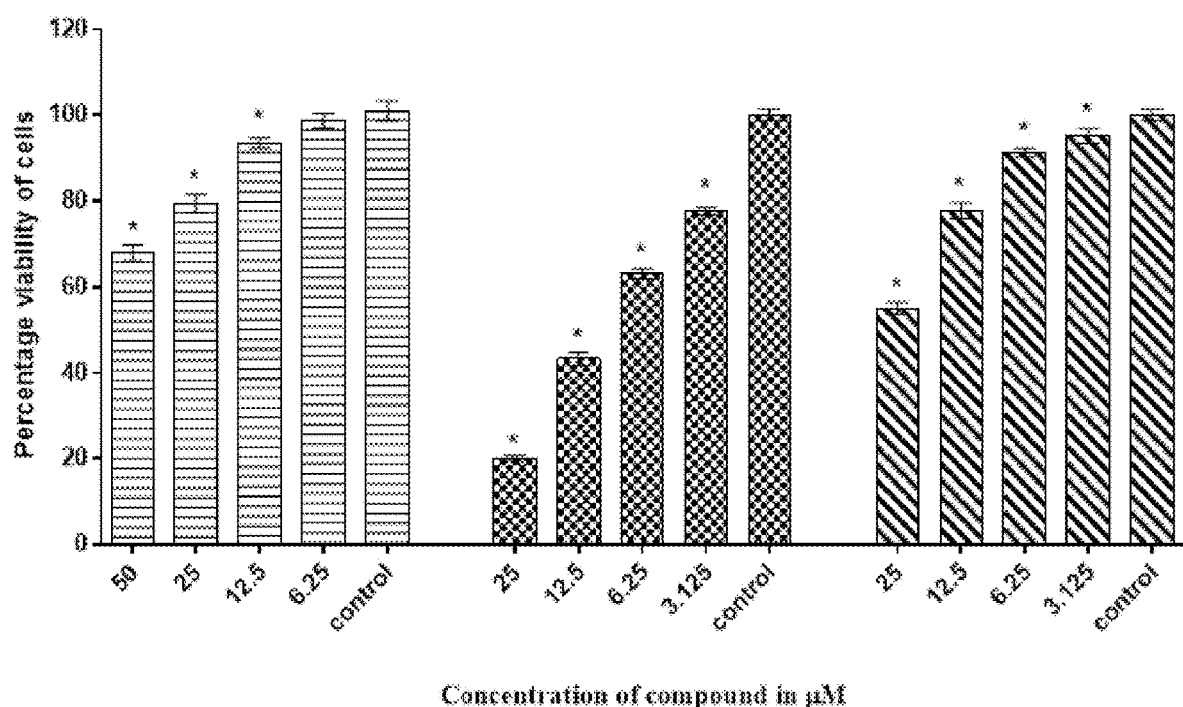
FIG. 7. Graph of cytotoxic effect of series complexes (0-2) concentrations on cell viability of HeLa cell line.
Figure 8:
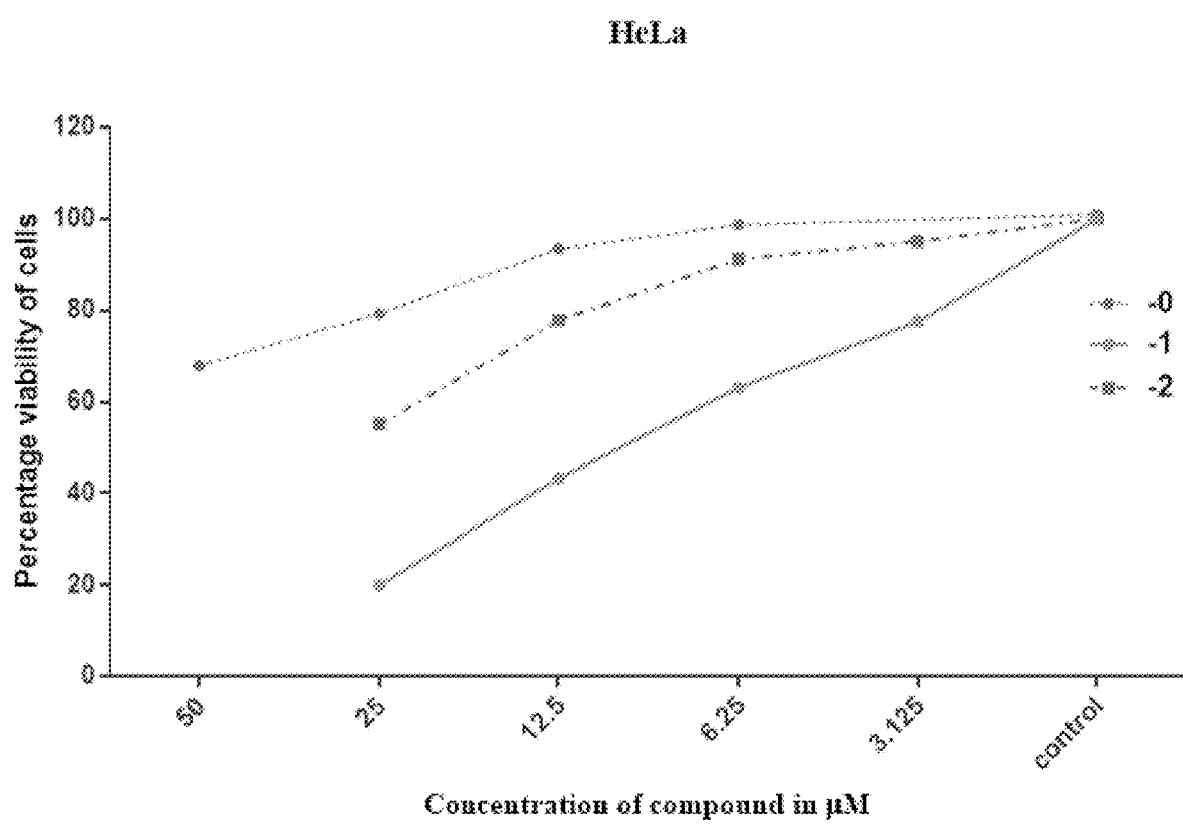
FIG. 8. In vitro cytotoxic effect of series complexes (0-2) concentrations on cell viability of HeLa cell line.
Figure 11A:
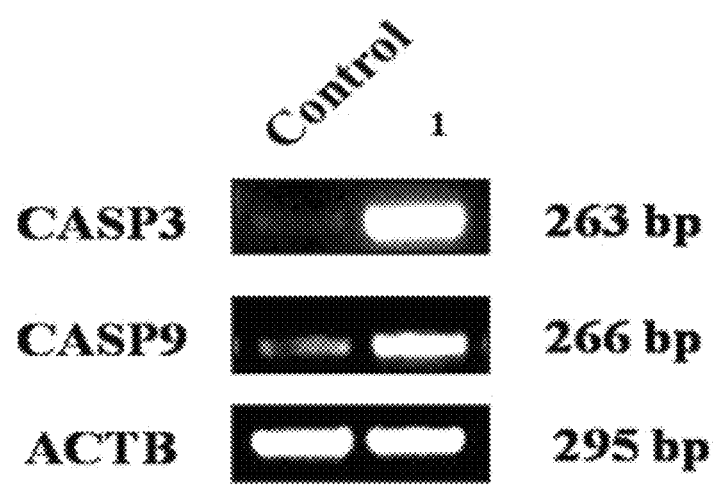
FIG. 11A: Representative reverse transcription-polymerase chain reaction (RT-PCR) showing β-actin, Caspase 3 and 9 gene expression in HCT-15 cells (Human Colon Carcinoma).
Figure 11B:
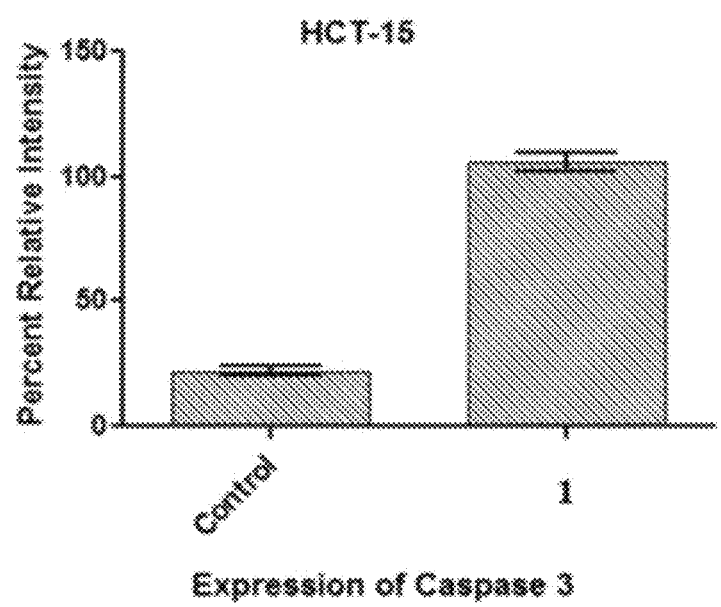
FIGS. 11B and 11C. Percent relative intensity measurement of caspase 3 (FIG. 11B) and 9 (FIG. 11C) expressions in RT-PCR for each group expressed as percentage of β-actin.
Figure 11C:
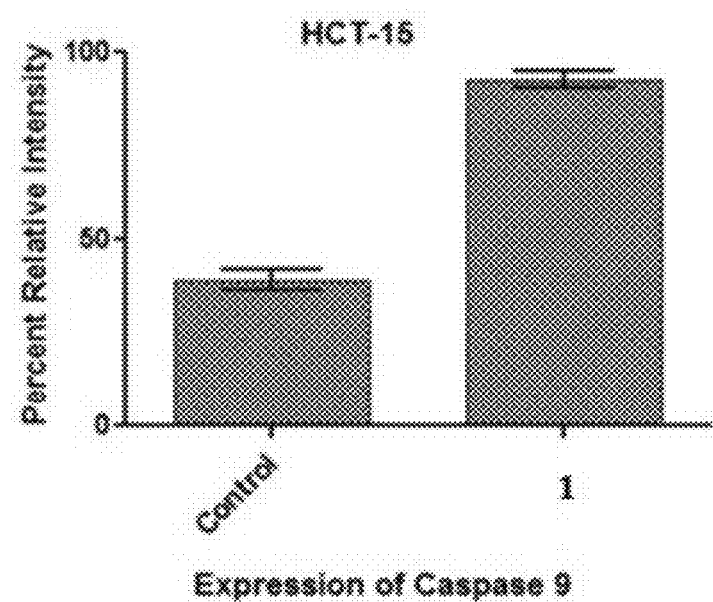
Figure 12A:
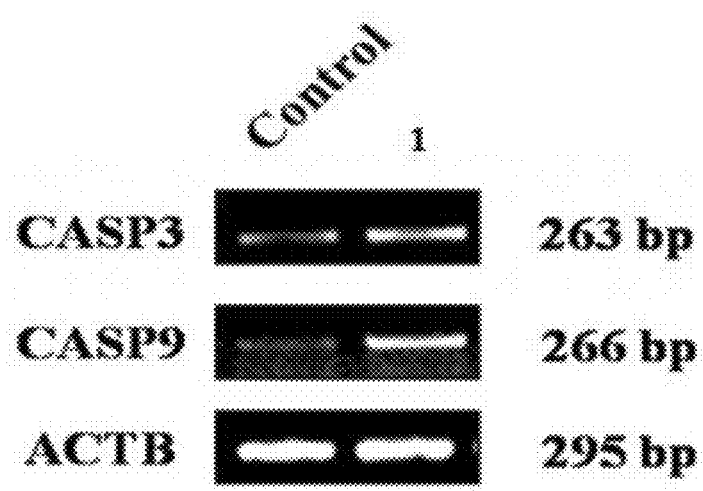
FIG. 12A. Representative reverse transcription-polymerase chain reaction (RT-PCR) showing β-actin, Caspase 3 and 9 gene expression in HeLa cells (Human Cervix Cancer).
Figure 12B:
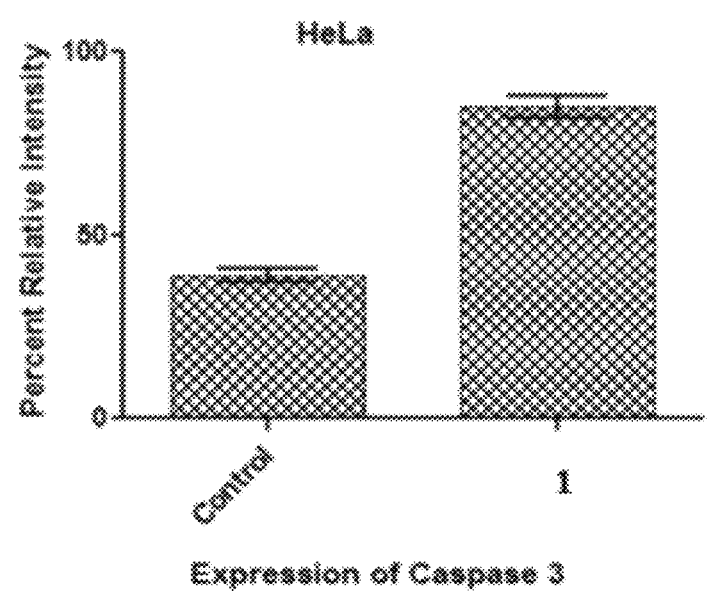
FIGS. 12B and 12C. Percent relative intensity measurement of caspase 3 (FIG. 12B) and 9 (FIG. 12C) expressions in RT-PCR for each group expressed as percentage of β-actin.
Figure 12C:
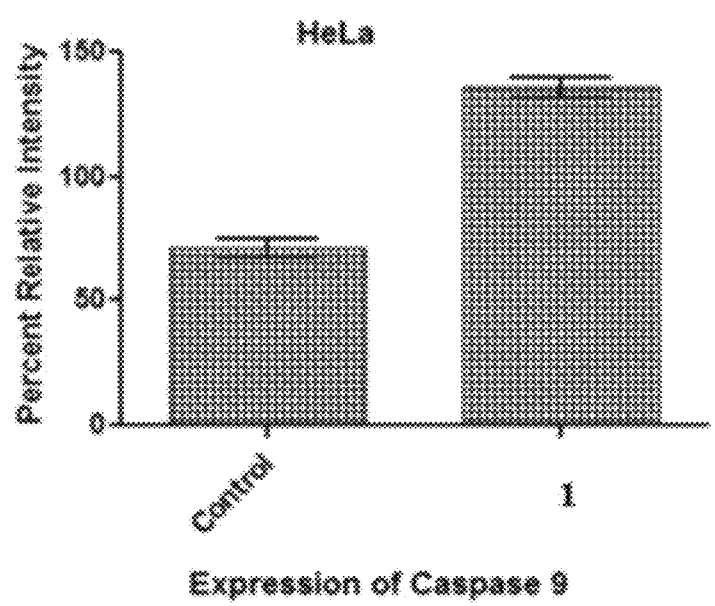
Figure 13A:
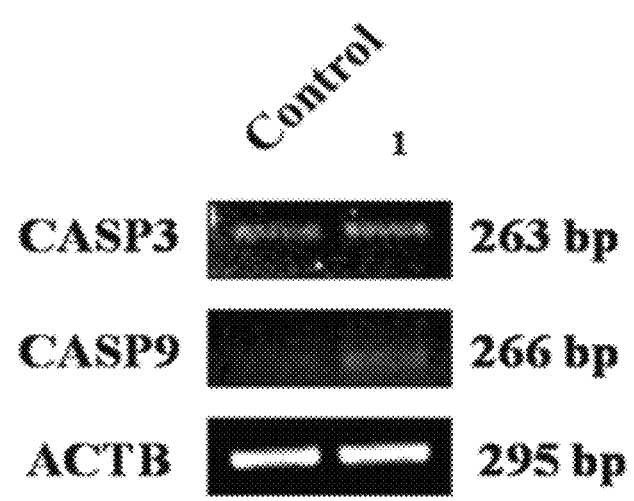
FIG. 13A. Representative reverse transcription-polymerase chain reaction (RT-PCR) showing β-actin, Caspase 3 and 9 gene expressions in MG-63 cells (Human Osteosarcoma).
Figure 13B:
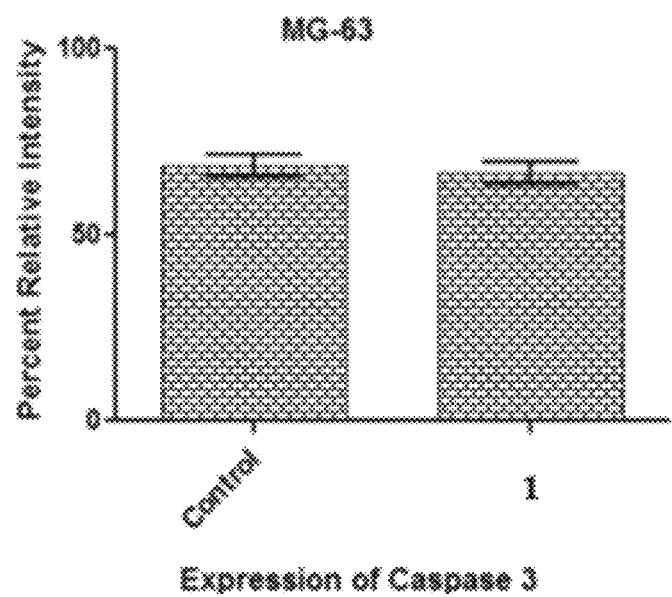
FIGS. 13B and 13C. Percent relative intensity measurement of caspase 3 (FIG. 13B) and 9 (FIG. 13C) expressions in RT-PCR for each group expressed as percentage of β-actin.
Figure 13C:
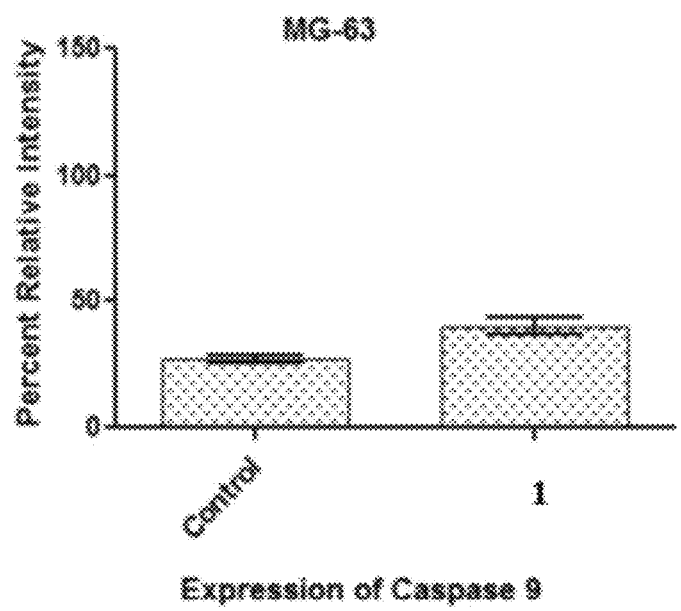
Figure 14:
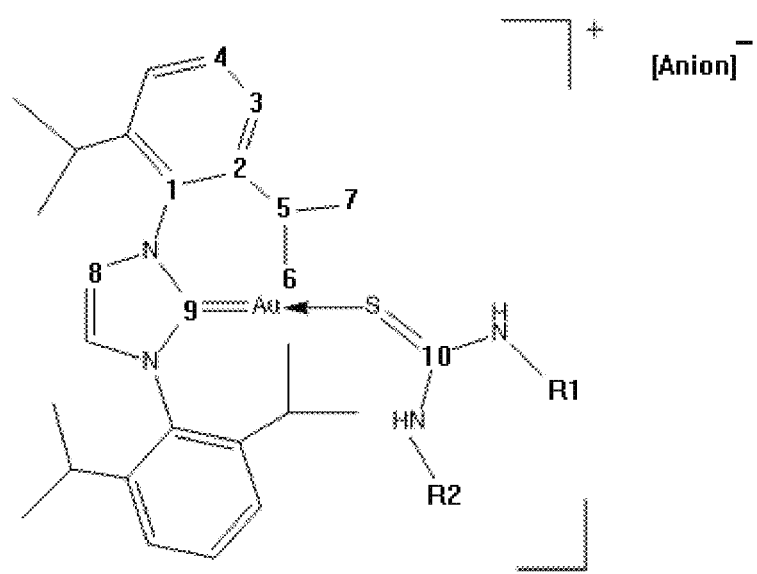
FIG. 14 Gold(I) complex of Formula (I).
Figure 15:
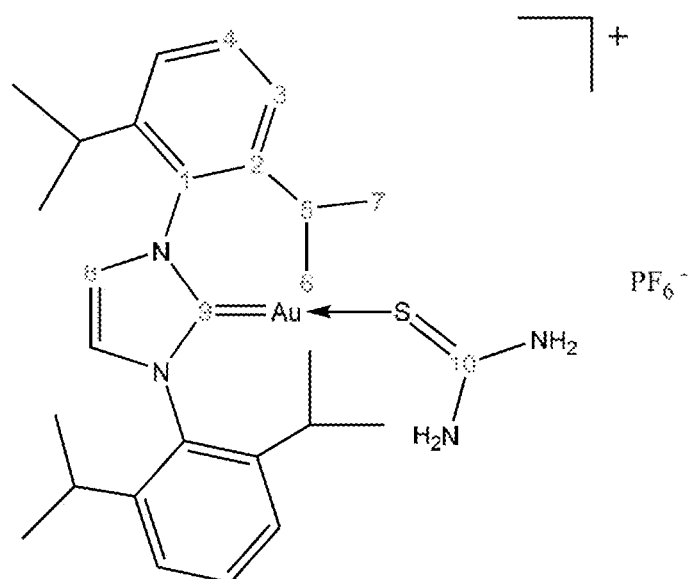
FIG. 15. Gold(I) complex (1).
Figure 16:
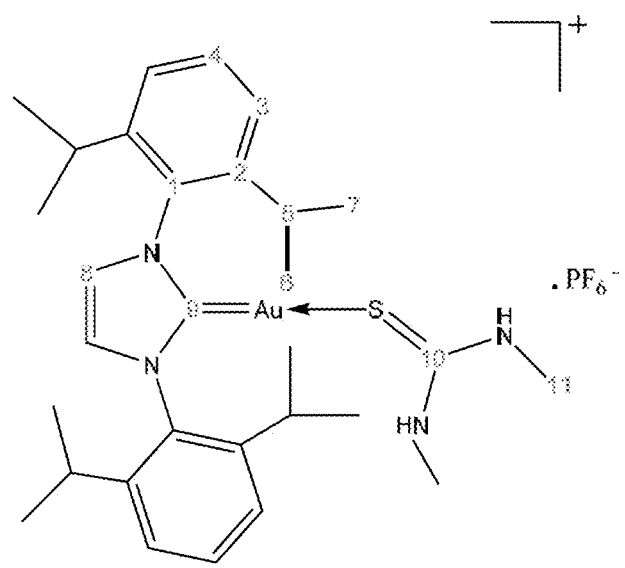
FIG. 16. Gold(I) complex (2).

The toxic attribute of complex (1) was further determined by studying the expression levels of the Caspase-3 and the Caspase-9 gene, and with the apoptotic markers at the mRNA level (FIGS. 11-13). The levels of both the caspases were measured as a percent relative intensity expression to β-actin of the respective groups. In comparison to the control group, the treatment with complex (1) of the HCT-15 and HeLa cells resulted in the induction of apoptosis and a significant upregulation in the expression of both caspase-3 and 9 was demonstrated at the mRNA level ($p<0.005$). However, no significant deviation in the expression of caspase-3 and 9 was noted in complex (1) and the control treated MG-63 cells (FIG. 5). The expression of the caspases in both the groups at the mRNA level is represented in the form of a histogram. The results represent the mode of the toxic effect of complex (1) in the HCT-15 and HeLa cells. The present results are in line with earlier studies representing the toxic attribute of gold complexes by the up-regulated expression of caspase-3 and caspase-9; see Y. Wang, Q. Y. He, R. W. Sun, C. M. Che, "Gold(III) porphyrin 1a induced apoptosis by mitochondrial death pathways related to reactive oxygen species," *Cancer Res.*, 2005, 56(24), 11553-64; O. Rackham, S. J. Nichols, P. J. Leedman, S. J. Berners-Price, A. Filipovska "Gold(I) phosphine complex selectively induces apoptosis in breast cancer cells: implications for anticancer therapeutics targeted to mitochondria. Biochemical pharmacology," *Biochem. Pharmacol.*, 2007, 74(7), 992-1002; I. Ott, X. Qian, Y. Xu, D. H. Vlecken, I. J. Marques, D. Kubutat, J. Will, W. S. Sheldrick, P. Jesse, A. Prokop, C. P. Bagowski, "A gold(I) phosphine complex containing a naphthalimide ligand functions as a TrxR inhibiting antiproliferative agent and angiogenesis inhibitor," *J. Med. Chem.*, 2009, 52(3), 763-70; and X. Cheng, P. Holenya, S. Can, H. Alborzinia, R. Rubbiani, I. Ott, S. Wölfl. "A TrxR inhibiting gold(I) NHC complex induces apoptosis through ASK1-p38-MAPK signaling in pancreatic cancer cells.," *Mol. Cancer*, 2014, 13(1), 221, each incorporated herein by reference in their entirety. However, complex (1) may have induced cell death by some other mechanisms in spite of the caspase-3 and 9 in the MG-63 cells.

As shown herein the inventors have synthesized, characterized, and demonstrated the in vitro cytotoxicity of complexes (1) and (2). The $^{13}C$ NMR solid state was used as a complementary technique to explore the stability of the complexes in a liquid and a solid state. Single crystal X-ray diffraction revealed that both complexes have a distorted linear geometry. Furthermore, complex (1) was found to be more potent as an anticancer agent than cisplatin against all human cancer cell lines. Both complexes showed great stability in an aqueous solution. Complex (1) interacted more with L-tryptophan than complex (2). A reduction in peak height and a peak current shift in potential were observed by the interaction of both complexes with L-tryptophan. The mode of toxic effect of complex (1) in the HCT-15 and HeLa cells induced the cells death by the up-regulated expression of caspase-3 and caspase-9. Complex (1) may have induced cell death by another or an additional mechanism in spite of the caspase-3 and 9 in the MG-63 cells.

Abbreviations

Me$_2$Tu=N,N'-dimethylthiourea, Tu=thiourea, IPr=1,3-Bis (2,6-di-isopropylphenyl)imidazol-2-ylidene, HeLa=cervical cancer cell line, HCT15=colon adenocarcinoma, MG-63=bone cancer cell line, NHC=N-hetero-cyclic carbene, DMEM=Dulbecco's Modified Eagle's Medium.

Terminology

Terminology used herein is for the purpose of describing particular embodiments only and is not intended to be limiting of the invention.

The headings (such as "Background" and "Summary") and sub-headings used herein are intended only for general organization of topics within the present invention, and are not intended to limit the disclosure of the present invention or any aspect thereof. In particular, subject matter disclosed in the "Background" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

As used herein, the singular forms "a", "an" and "the" are intended to include the plural forms as well, unless the context clearly indicates otherwise.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

As used herein, the term "and/or" includes any and all combinations of one or more of the associated listed items and may be abbreviated as "/".

Links are disabled by deletion of http: or by insertion of a space or underlined space before www. In some instances, the text available via the link on the "last accessed" date may be incorporated by reference.

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values), etc. Any numerical range recited herein is intended to include all sub-ranges subsumed therein.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it also describes subranges for Parameter X including 1-9, 1-8, 1-7, 2-9, 2-8, 2-7, 3-9, 3-8, 3-7, 2-8, 3-7, 4-6, or 7-10, 8-10 or 9-10 as mere examples. A range encompasses its endpoints as well as values inside of an endpoint, for example, the range 0-5 includes 0, >0, 1, 2, 3, 4, <5 and 5.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present invention that do not contain those elements or features.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Spatially relative terms, such as "under", "below", "lower", "over", "upper", "in front of" or "behind" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the 8s is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears.

The citation of references herein does not constitute an admission that those references are prior art or have any relevance to the patentability of the technology disclosed herein. Any discussion of the content of references cited is intended merely to provide a general summary of assertions made by the authors of the references, and does not constitute an admission as to the accuracy of the content of such references.

The invention claimed is:

1. A gold(I) complex having the following chemical structure:

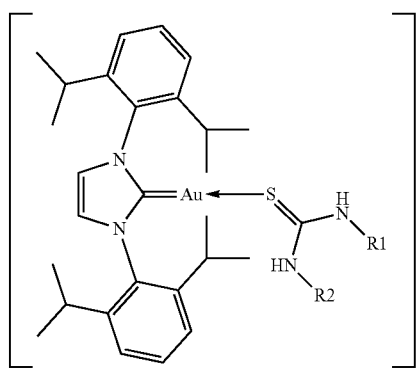

wherein [Anion]− is selected from the group consisting of fluoride, chloride, iodide, triflate, and hexafluorophosphate ("$PF_6$"), and wherein R1 and R2 are, independently, hydrogen, $C_{1-6}$ alkyl, $C_{2-6}$ alkenyl, $C_{2-6}$ alkynyl, or $C_{6-10}$ aryl.

2. The gold(I) complex of claim 1, wherein R1 and R2 are each hydrogen.

3. The gold(I) complex of claim 1, wherein R2 and R2 are each methyl.

4. The gold(I) complex of claim 1, wherein the anion is fluoride, chloride, iodide, or triflate.

5. The gold(I) complex of claim 1, wherein the anion is hexafluorophosphate ("$PF_6$").

6. The gold(I) complex of claim 1 that is complex (1) [Au(Ipr)(κSCN$_2$H$_4$)]PF$_6$.

7. A sterile pharmaceutical composition comprising at least one gold(I) complex of claim 1 and at least one pharmaceutically acceptable carrier or excipient.

8. The gold(I) complex of claim 1 that is complex (2)[Au(Ipr)(κSCN$_2$C$_2$H$_8$)PF$_6$.

* * * * *